United States Patent [19]
Kriesel et al.

[11] Patent Number: 5,372,578
[45] Date of Patent: * Dec. 13, 1994

[54] LIQUID DELIVERY APPARATUS

[75] Inventors: Marshall S. Kriesel, St. Paul; Thomas N. Thompson, Richfield, both of Minn.

[73] Assignee: Science Incorporated, Bloomington, Minn.

[*] Notice: The portion of the term of this patent subsequent to May 24, 2011 has been disclaimed.

[21] Appl. No.: 53,722

[22] Filed: Jun. 17, 1993

Related U.S. Application Data

[63] Continuation-in-part of Ser. No. 870,403, Apr. 17, 1992.

[51] Int. Cl.$^5$ ............................................. A61M 5/00
[52] U.S. Cl. ............................................. 604/8; 604/9
[58] Field of Search ............... 604/8, 9, 10, 247, 175, 604/181, 183, 186, 891, 246, 248

[56] References Cited

U.S. PATENT DOCUMENTS

| | | | |
|---|---|---|---|
| 4,681,560 | 7/1987 | Schulte | 604/8 |
| 4,761,158 | 8/1988 | Schulte | 604/8 |
| 4,781,672 | 11/1988 | Hoover | 604/9 |
| 4,816,016 | 3/1989 | Schulte | 604/8 |
| 4,979,937 | 12/1990 | Khorasuni | 604/8 |
| 4,995,856 | 2/1991 | Heindl | 604/8 |
| 5,084,015 | 1/1992 | Moriuchi | 604/9 |

*Primary Examiner*—Michael A. Brown
*Attorney, Agent, or Firm*—J. E. Brunton

[57] ABSTRACT

A liquid delivery apparatus including a housing having internal walls that define a chamber, a support disposed within the housing and having a central portion, an edge portion circumscribing the central portion and including a liquid passageway in communication with the chamber of the housing. The liquid passageway has an inlet and an outlet.

14 Claims, 14 Drawing Sheets

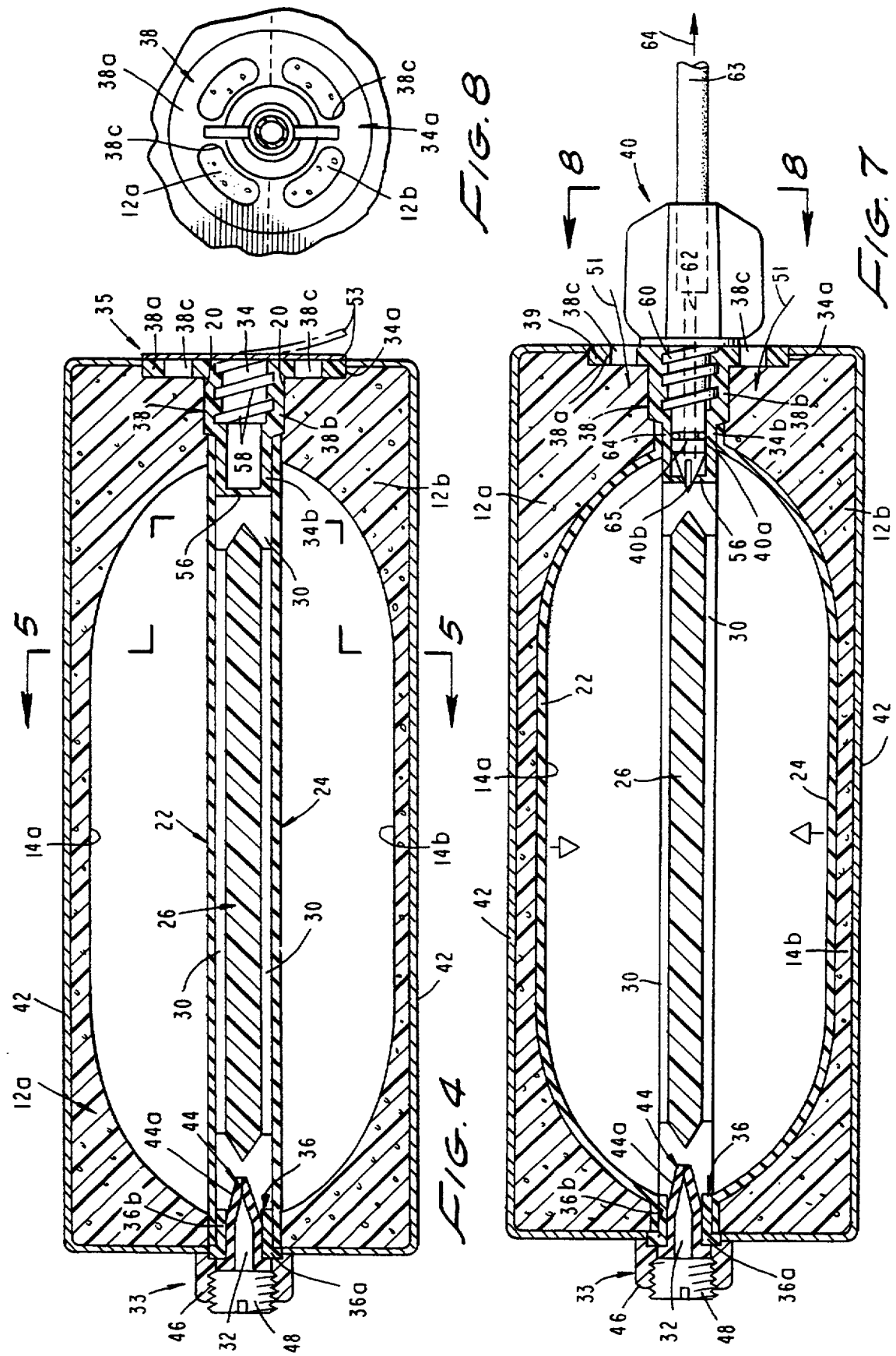

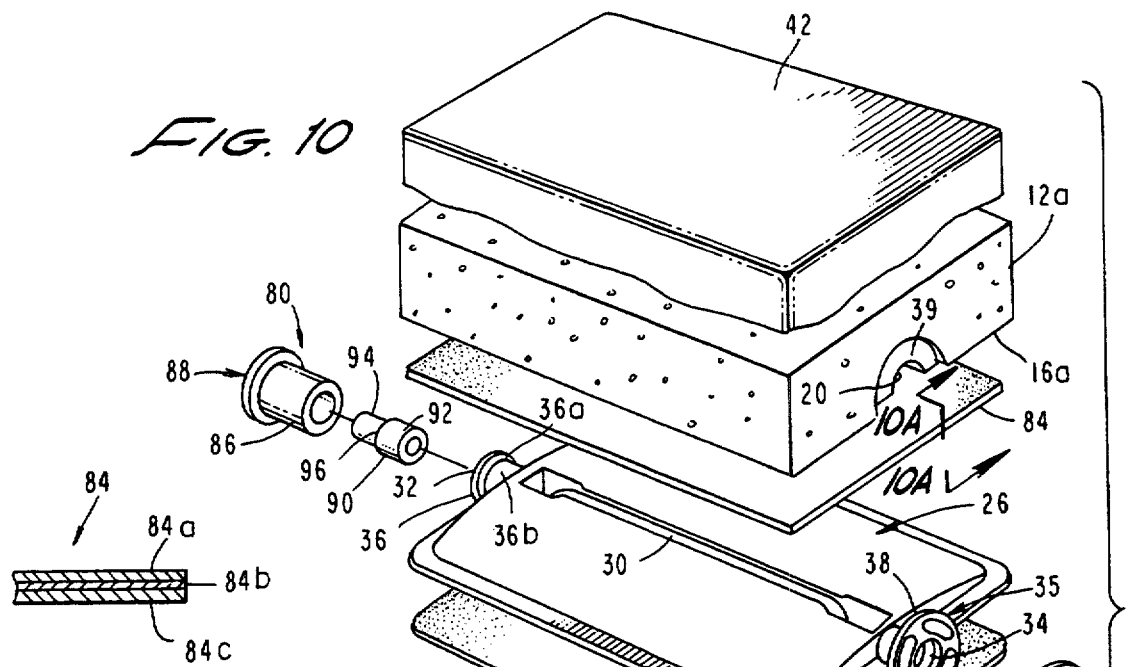
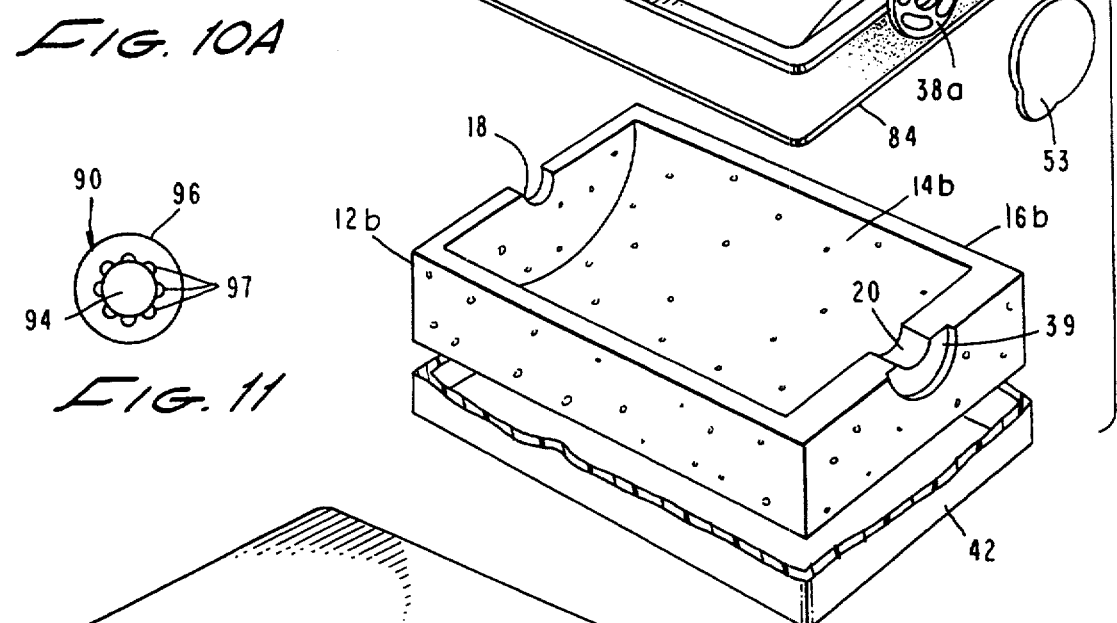
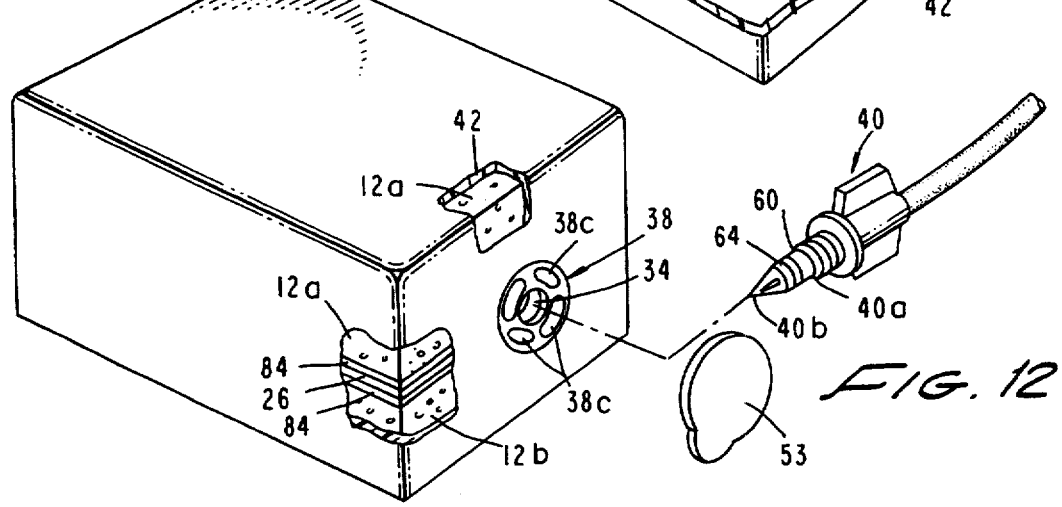

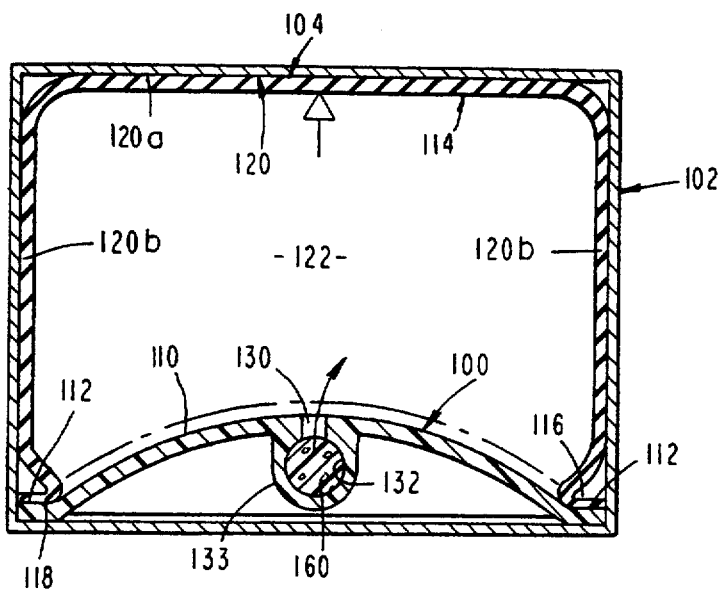
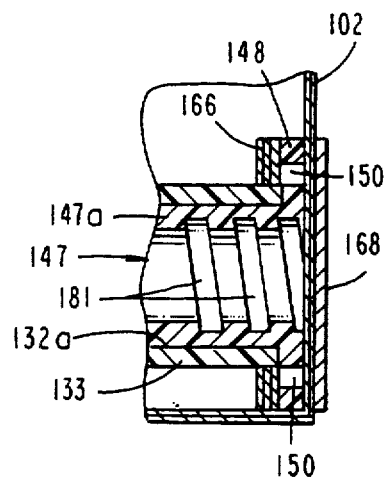
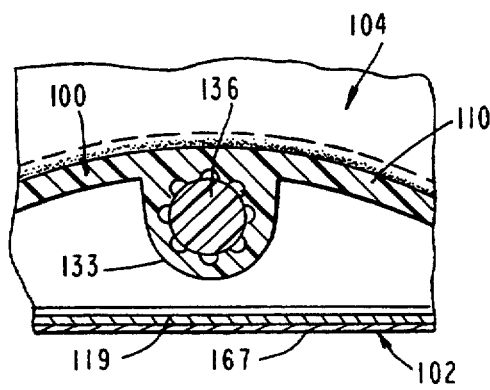
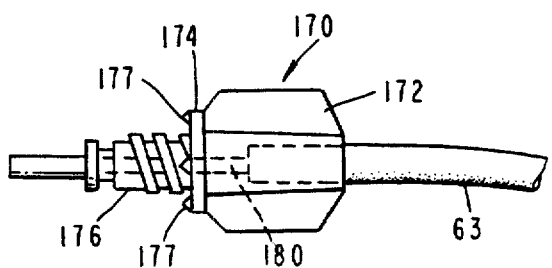
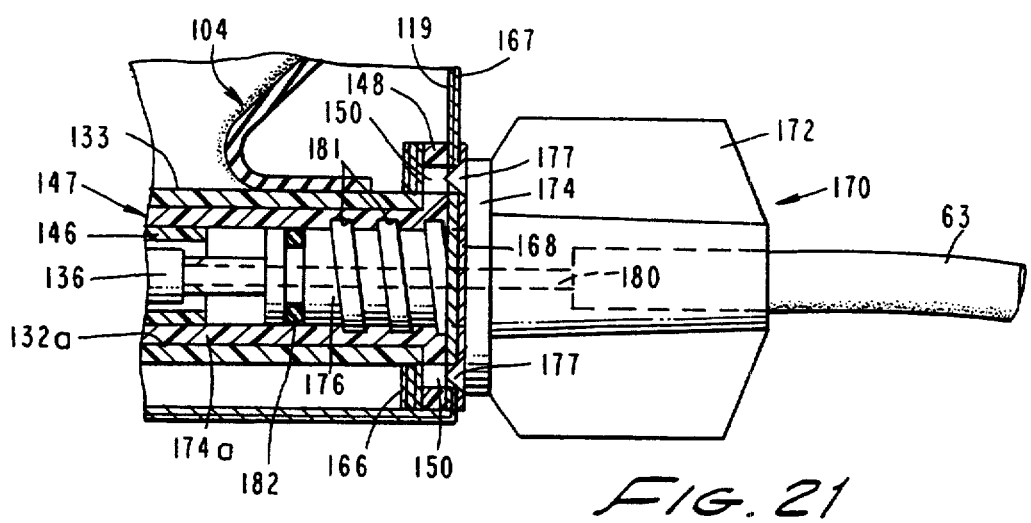

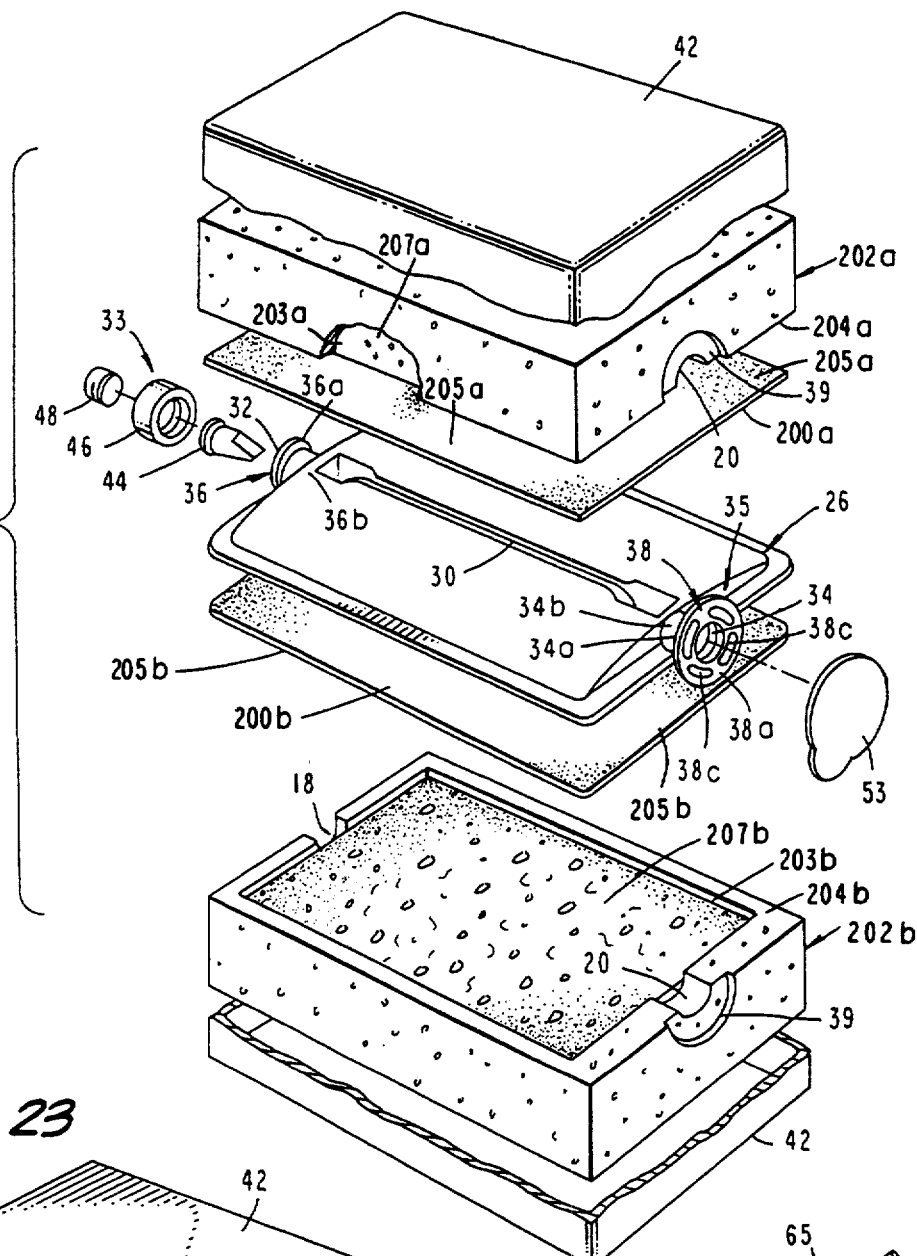
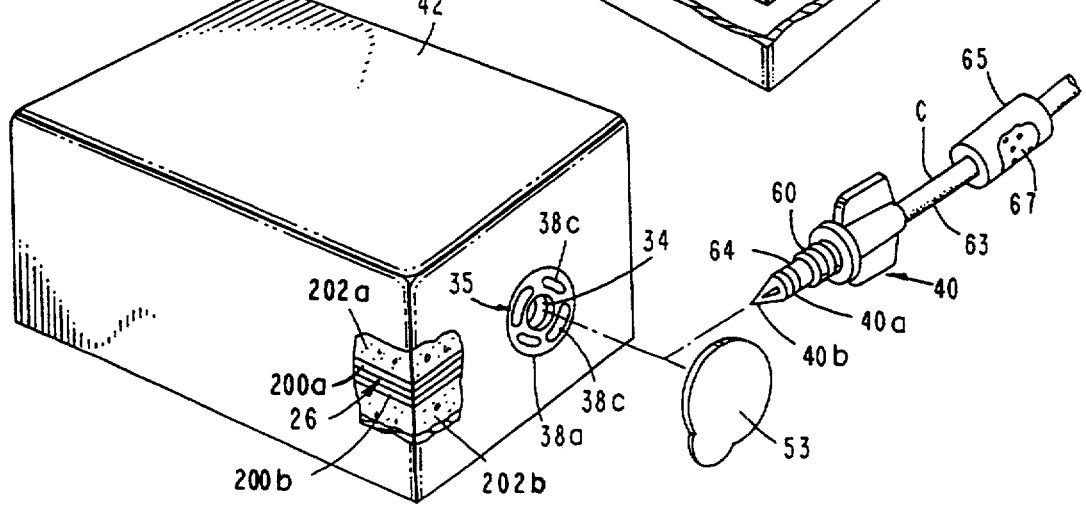

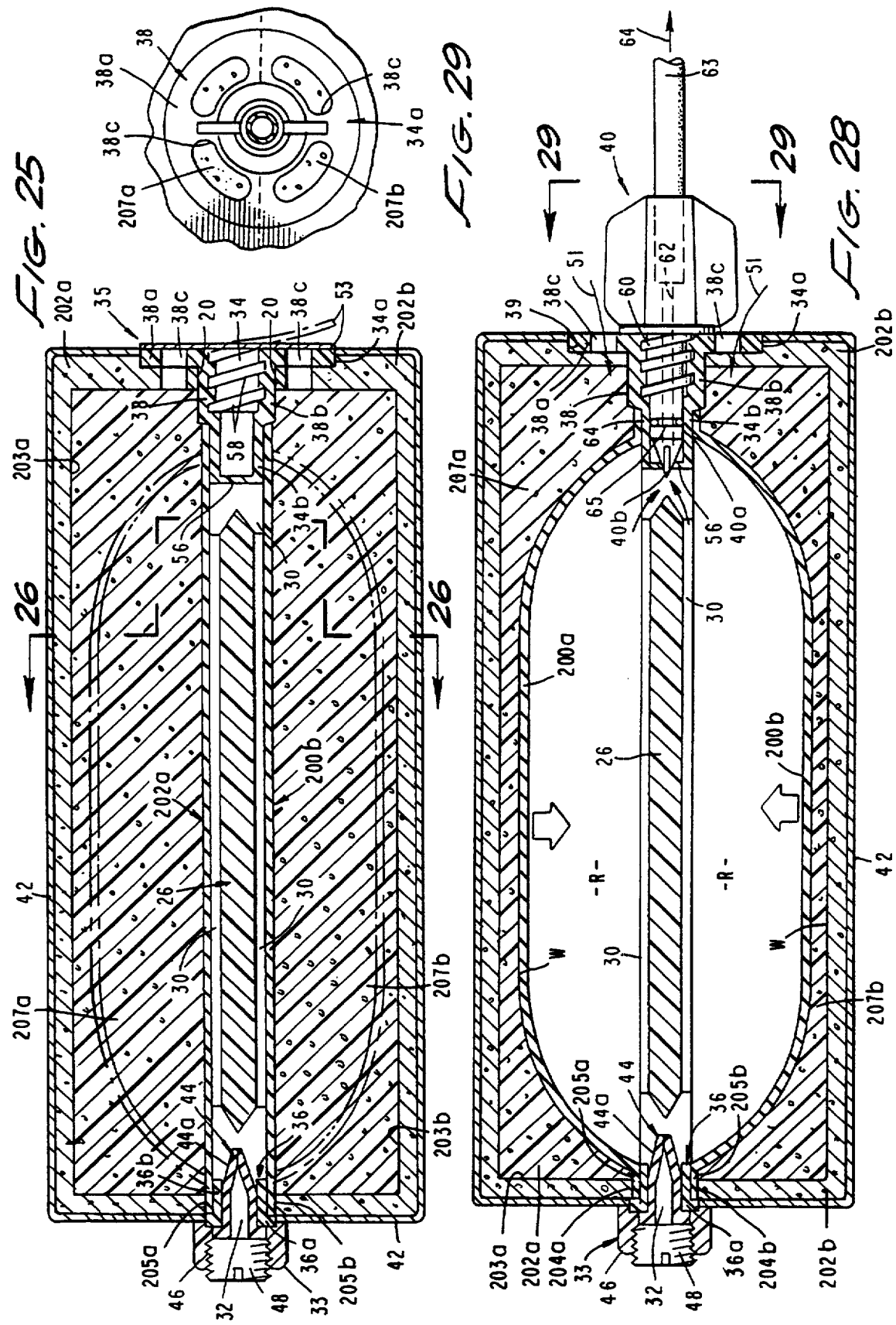

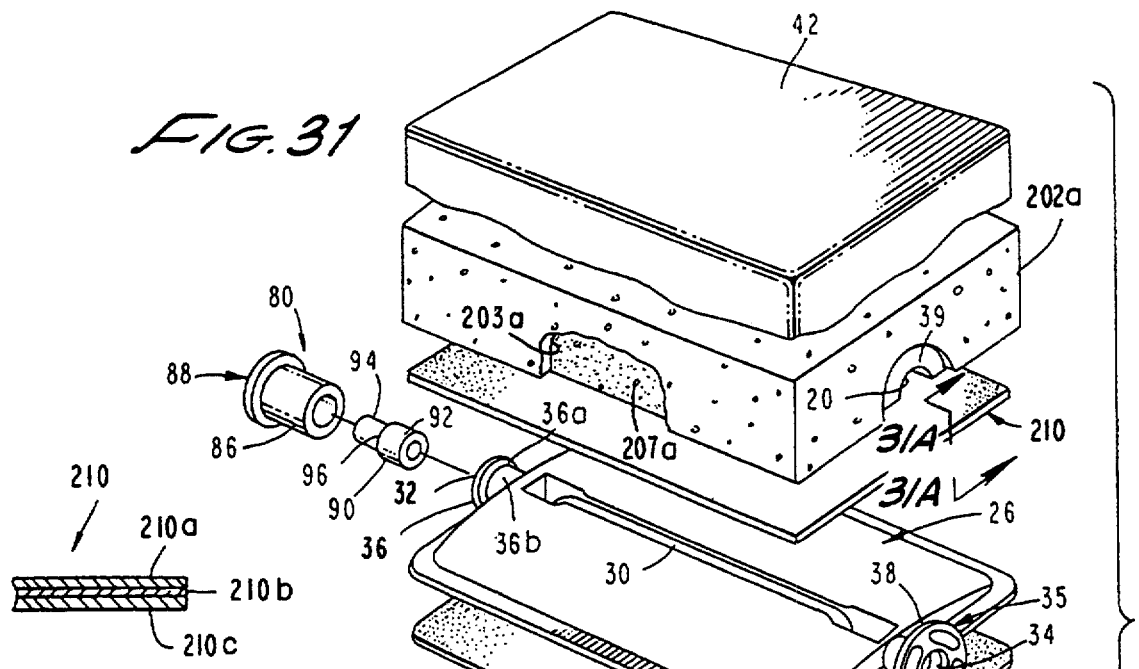
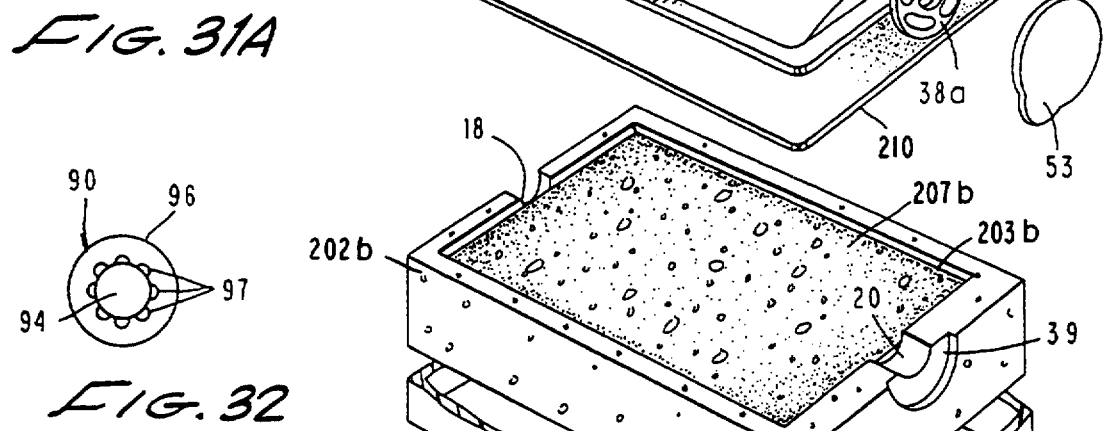
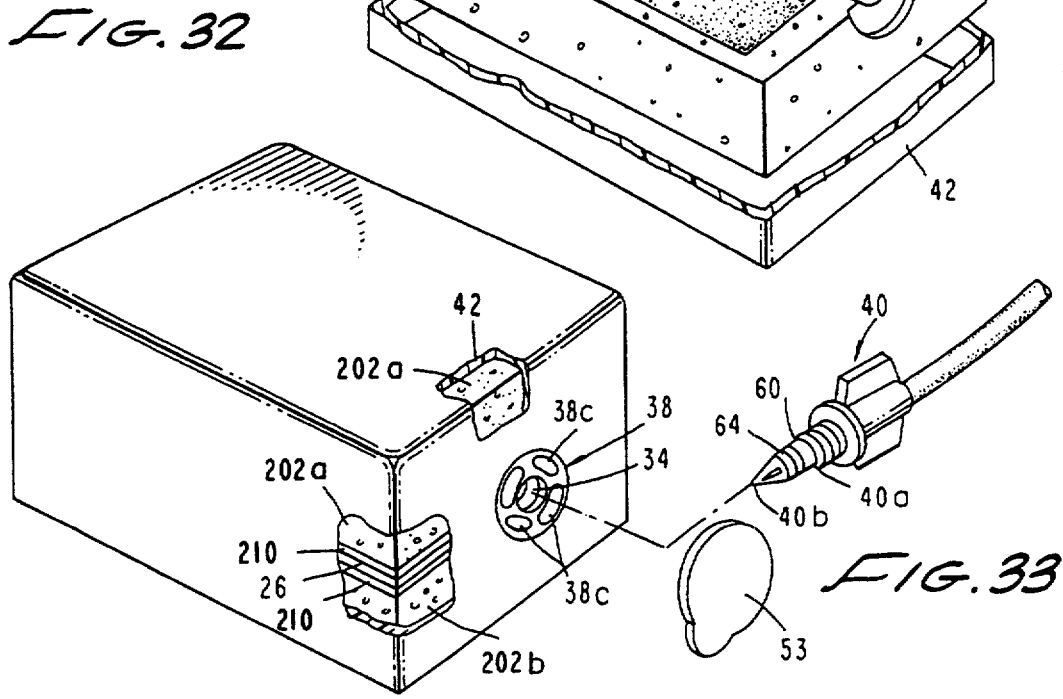

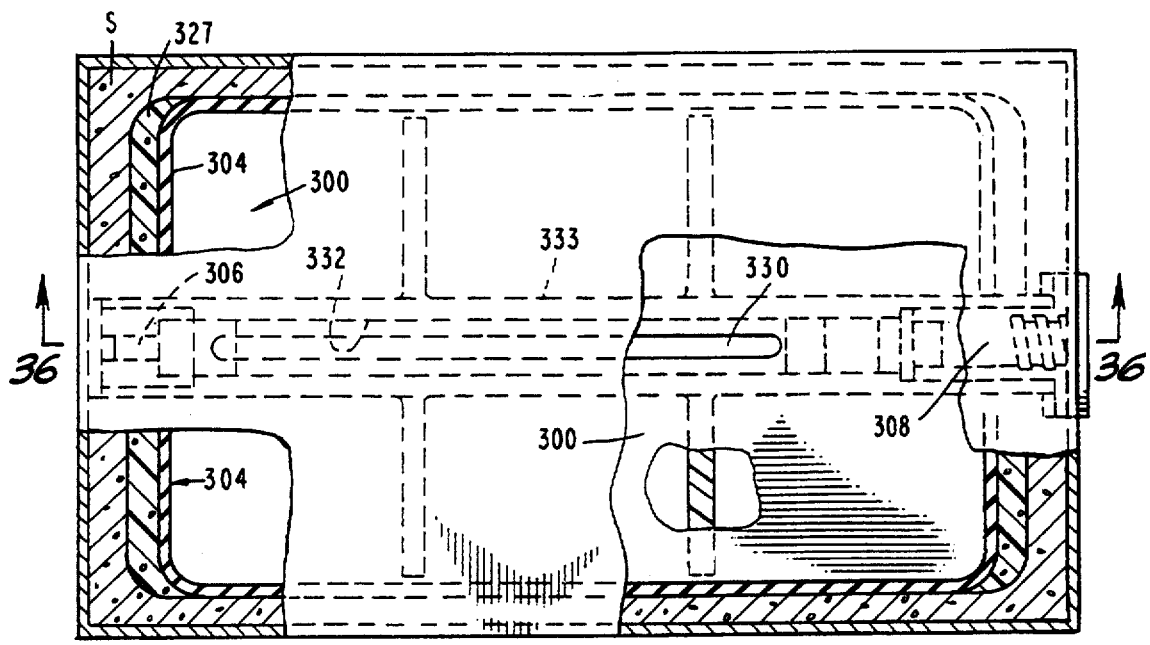
FIG. 35
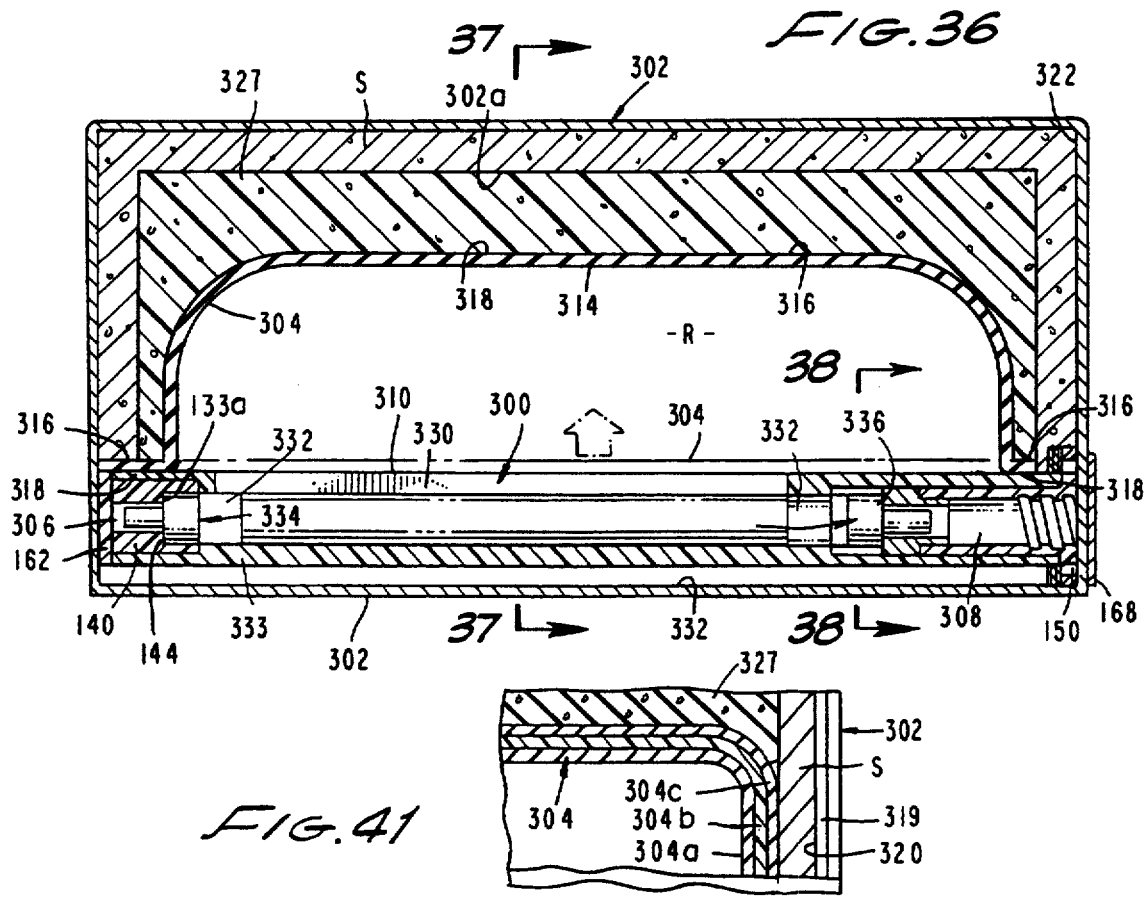
FIG. 36
FIG. 41

LIQUID DELIVERY APPARATUS

BACKGROUND OF THE INVENTION

This is a continuation-in-part of copending application U.S. Ser. No. 07/870,403 filed Apr. 17, 1992.

FIELD OF THE INVENTION

The present invention relates generally to liquid delivery systems. More particularly, the invention concerns an apparatus for enteral feeding applications.

DISCUSSION OF THE INVENTION

When patients are comatose, or for some reason are unable to take nourishment by mouth, enteral feeding becomes necessary. Enteral nutrition, or tube feeding, is typically accomplished by nasogastric administration or by direct delivery of liquids to the stomach via a surgically implanted feeding tube. Parastalic pumps are currently used for nasogastric feeding when gravity flow from an elevated container is insufficient to instill flow or when an exact amount of regulated feeding is necessary. Such devices are cumbersome to use and at times have proven unreliable.

The apparatus of the present invention overcomes the drawbacks of prior art enteral feeding systems by providing a self-contained apparatus which includes an internal energy source that automatically expels prepackaged nutritional liquids from a sealed aseptic container at a desired uniform rate.

Aseptic packaging is, of course, not new. Such packaging is being used more and more in the food industry for packaging fruit juice, milk products and the like. Additionally, some use of aseptic packaging has been made in the medical field for packaging medical solutions.

When the packaged, aseptically filled liquid is a food product, such as fruit juice, the sealed package is typically punctured at a specific site location and the juice is withdrawn through a straw. When the packaged liquid is a medical solution, the package is typically opened, mixed with other components when required and emptied into a traditional, wide-mouth flexible bag solution container for enteral delivery by conventional gravity means and parastalic pump. However, in U.S. Pat. No. 4,826,500 issued to Rantsola, a system for the enteral delivery of a medical solution directly from an aseptic container is there described. In accordance with the methods of the Rantsola patent, the solution is passed from a container through an elongated giving set and metering system into a nasal tube. The container is an aseptic carton having penetrable side walls, with the giving set being provided with a fitting having a fluid passage extending therethrough. The fitting terminates at a carton cooperating portion which includes a first portion for penetrating the carton side walls to form an orifice therein, the orifice establishing fluid communication between the carton interior and the fitting fluid passage, and a second portion for engaging the carton side wall to maintain cooperation between the carton and fitting.

In U. S. Pat. No. 4,688,595, issued to Srebnik, et al, there is described an enteral nutrition delivery system which comprises an integral molded plastic base which includes a first platform to which is secured an infusion pump and a second platform having a recess in which is secured a specially designed bottle containing nutritional fluid to be fed to a patient. A tubing net-work is included for interconnecting the pump, bottle and the patient.

Neither Rantsola nor Srebnik, et al disclose or remotely suggest the novel apparatus of the present invention, which comprises a prefilled, self-contained system, including a unique stored energy source disposed within an aseptic package for delivering the nutritional liquid at a controlled, uniform rate.

Through use of the novel apparatus of the present invention, the disadvantageous current practice of preparing the dry nutrient composition and mixing it with sterile water at the point of use is avoided. The current practice of preparing the dry nutrient composition and mixing with sterile water at point of use has many obvious disadvantages. Historically, the use of this two-step method of treatment preparation has, in part, been driven by the problems resulting from combined solution sterilization, including chemical reactivity of certain nutrient materials under autoclave conditions because of the flexible bag. Prior art practices also typically employ intermittent feeding of the patient. Recent clinical practice now favors continuous feeding rather than intermittent feeding in most cases. In accordance with the present invention, certain drugs, minerals, nutrients and the like are aseptically sealed in a multi-barrier layer, oxygen impermeable, moisture-proof, microorganism-impermeable aseptic dispenser for automatic, on-demand continuous delivery to the patient without the required use of a parastalic pump or external energy sources of any kind.

SUMMARY OF THE INVENTION

It is an object of the present invention to provide a self-contained system for the enteral delivery of a nutrient solution from an aseptic package without the intermediate step of emptying the package into a traditional flexible bag solution container for delivery by parastalic pump, gravity means or the like.

More particularly, it is an object of the invention to provide a system of the aforementioned character in which an integral, inherently sterile, flat film energy source is contained within the aseptic package for automatically delivering on demand the premixed solution contained within the package to the patient at a precisely controlled rate.

Another object of the invention is to provide an aseptic carton having a non-permeable oxygen barrier with a penetrating portion for sealable penetration by a fitting having a fluid passageway therethrough in communication with a giving set.

Another object of the invention is to provide a carton as described in the preceding paragraph in which provision is made for ingress of make-up air so that an even outflow of solution to the patient is precisely maintained.

Another object of the invention is to provide a carton which utilizes a paper-board barrier laminated structure that maintains an isolated gas environment within the container.

Still another object of the invention is to provide a system of the class described in which the aseptic container and flat film integral energy source, or elastomeric membrane, can be economically mass produced at low cost to permit the discard of the assembly after use.

BRIEF DESCRIPTION OF THE DRAWINGS

FIG. 4 is a cross-sectional view taken along lines 4—4 of FIG. 3.

FIG. 7 is a cross-sectional view similar to FIG. 4 but illustrating the appearance of the apparatus when filled with fluid.

FIG. 8 is a fragmentary view taken along lines 8—8 of FIG. 7.

FIG. 10 is a generally perspective exploded view of an alternate form of the apparatus of the invention.

FIG. 10A is a cross-sectional view taken along lines 10A—10A of FIG. 10.

FIG. 11 is a cross-sectional view of the check valve assembly of FIG. 10.

FIG. 12 is a generally perspective view of the apparatus of FIG. 10 partly broken away to show internal construction and exploded to show the manner of interconnection of the delivery spike.

FIG. 16 is a cross-sectional view taken along lines 16—16 of FIG. 15.

FIG. 17 is a cross-sectional view taken along lines 17—17 of FIG. 15.

FIG. 18 is an enlarged fragmentary view of the outlet portion of the device.

FIG. 19 is an enlarged fragmentary view of the delivery spike of this latest embodiment.

FIG. 21 is an enlarged fragmentary cross-sectional view of the delivery spike mated with the outlet port assembly of the device.

FIG. 22 is a generally perspective exploded view of another form of the nutrient delivery apparatus of the present invention.

FIG. 23 is a perspective view of the apparatus of FIG. 22 partly broken away to show internal construction and exploded to show the manner of interconnection of the liquid delivery spike.

FIG. 25 is a cross-sectional view taken along lines 25—25 of FIG. 24.

FIG. 28 is a cross-sectional view similar to FIG. 25 but illustrating the appearance of the apparatus when filled with fluid.

FIG. 29 is a fragmentary view taken along lines 29—29 of FIG. 28.

FIG. 31 is a generally perspective exploded view of still another alternate form of the apparatus of the invention.

FIG. 31A is a cross-sectional view taken along lines 31A—31A of FIG. 31.

FIG. 32 is a cross-sectional view of the check valve assembly of FIG. 31.

FIG. 33 is a generally perspective view of the apparatus of FIG. 31 partly broken away to show internal construction and exploded to show the manner of interconnection of the delivery spike.

FIG. 35 is a plan view of the device partly broken away to show internal construction.

FIG. 36 is a cross-sectional view taken along lines 36—36 of FIG. 35.

FIG. 41 is a fragmentary cross-sectional view showing the construction of the deformable members and of the multifilm barrier construction of this latest embodiment.

DESCRIPTION OF THE INVENTION

Figure 1:
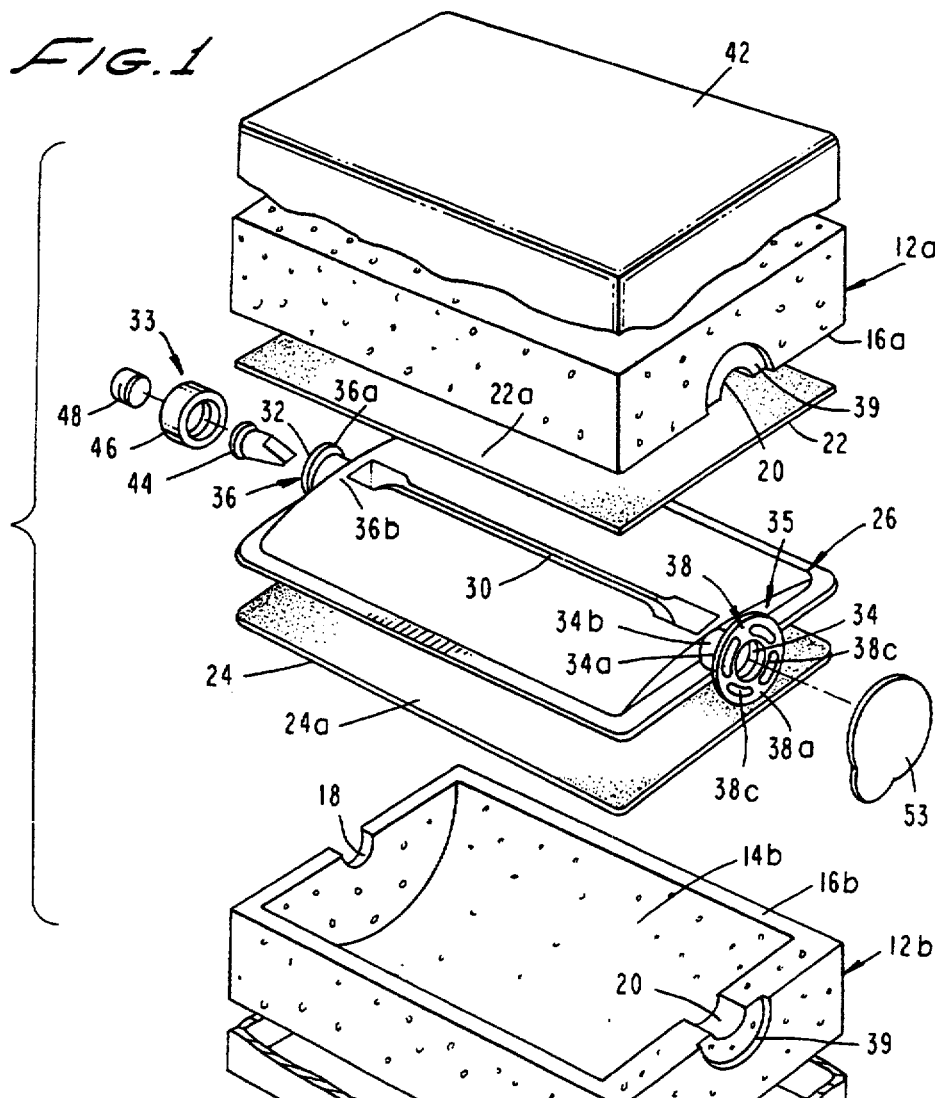
FIG. 1 is a generally perspective exploded view of the nutrient delivery apparatus of the present invention.
Figure 2:
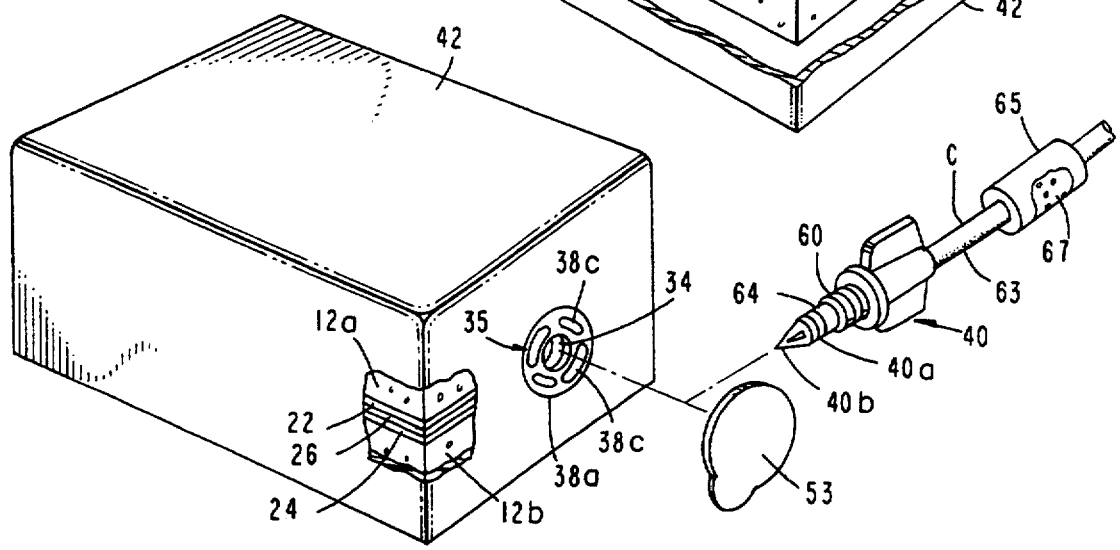
FIG. 2 is a perspective view of the apparatus partly broken away to show internal construction and exploded to show the manner of interconnection of the liquid delivery spike.
Figure 3:
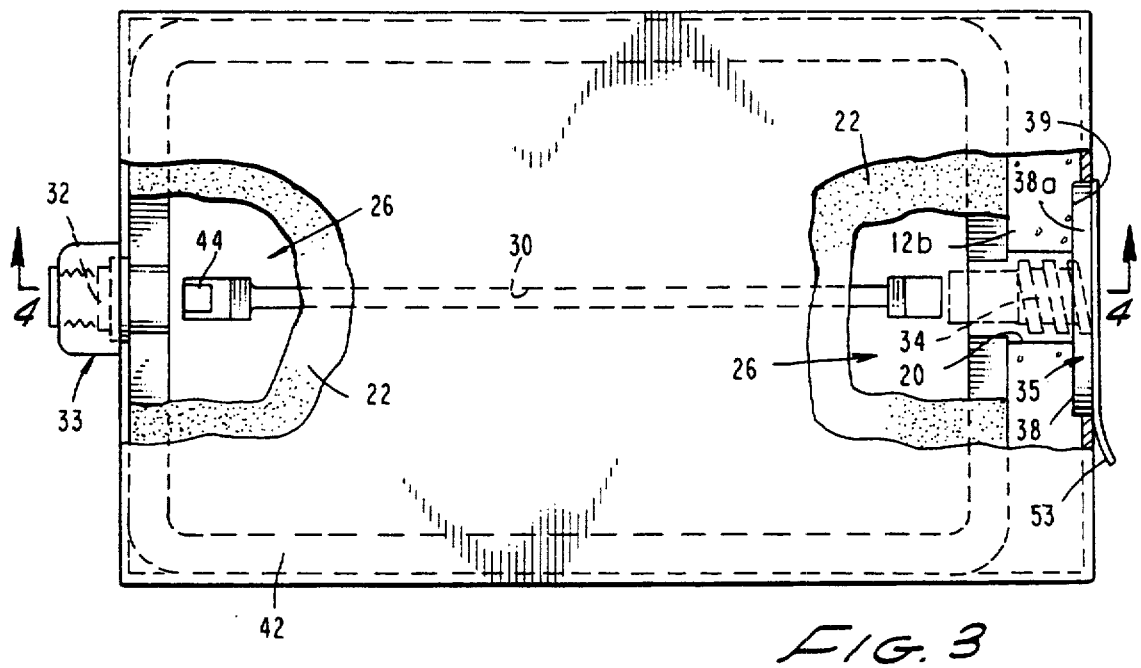
FIG. 3 is a top-plan view of the device partly broken away to show internal construction.

Referring to the drawings and particularly to FIGS. 1, 2 and 3, the liquid delivery apparatus of the present invention comprises a body made up of cooperating first and second portions 12a and 12b respectively. As can best be seen by referring to FIG. 5, each body portion 12a and 12b includes internal walls defining cavities 14a and 14b respectively with each cavity being circumscribed by an edge 16a and 16b respectively. Each body portion is also provided at either end with semi-circular shaped, indexable openings generally designated by the numerals 18 and 20.

A first distendable membrane 22 is provided with an edge portion 22a which is disposed in engagement with edge portion 16a of first body portion 12a. A second distendable membrane 24 having an edge portion 24a is disposed in engagement with edge portion 16b of second body portion 12b. Each of the distendable membranes 22 and 24, the unique character of which will presently be described, includes a central portion 22b and 24b respectively which spans the cavity of the body portion with which the membrane is associated (FIG. 5).

Disposed between distendable membranes 22 and 24 is a rigid support, or ullage member 26. Support member 26, which can be constructed from any suitable plastic such as polypropylene, polystyrene, polyethylene, or polycarbonate, is provided with a longitudinally extending fluid passageway 30 which is in communication at one end with a fluid inlet port 32 of an inlet port assembly 33 and is in communication at its opposite end with a fluid outlet port 34 of an outlet port assembly 35. Fluid inlet port assembly 33 includes an inlet adapter 36 having a flange portion 36a and a neck portion 36b which is closely received within apertures 18 provided in body portions 12a and 12b. Similarly, outlet port 34 includes a flange portion 34a and a neck portion 34b which portion is closely received within apertures 20 provided in body portions 12a and 12b. It is to be noted that body portions 12a and 12b are also provided with semicircular shaped recessed portions 39 which are adapted to closely receive flange portion 38a of outlet port adapter 38 which in this form of the invention comprises a port of the vent means for permitting the flow of gases between atmosphere and the interior of the liquid delivery apparatus.

Also comprising a part of the liquid delivery apparatus of the form of the invention shown in the drawings is a fluid delivery means which is in communication with the fluid outlet port of the apparatus. In a manner presently to be described, the fluid delivery means functions to deliver fluid to the patient. This fluid delivery means is shown in FIG. 2 as comprising a delivery spike assembly 40, which is adapted to cooperate with the fluid outlet port assembly 35.

Figure 5:
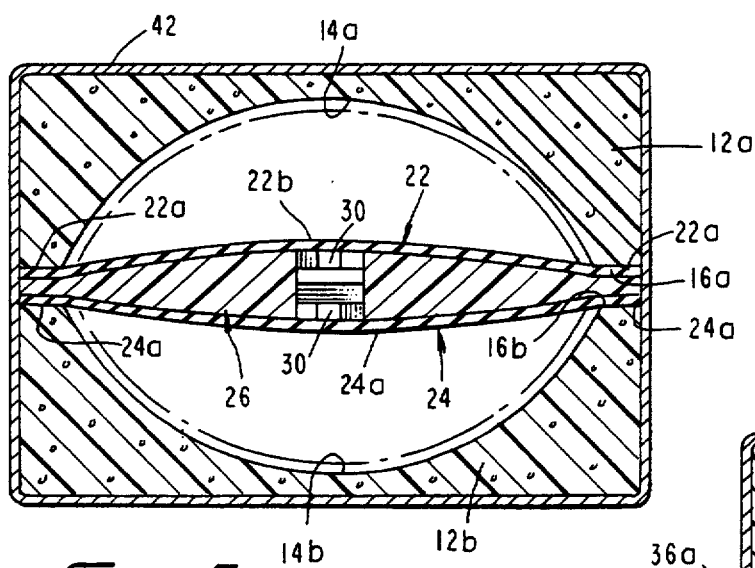
FIG. 5 is a cross-sectional view taken along lines 5—5 of FIG. 4.
Figure 9:
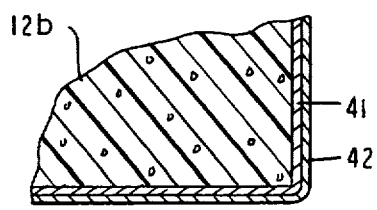
FIG. 9 is a fragmentary cross-sectional view illustrating one form of the multi-film barrier construction of the device.

As best seen by referring to FIGS. 2 and 5, body portions 12a and 12b are encapsulated by oxygen nonpermeable encapsulating barrier means shown here as thin layers of material 41 and 42 sealably surrounding body portions 12a and 12b (FIG. 9). The character of this sealing material and the manner in which it is applied will be discussed hereinafter.

Receivable within fluid filling inlet adapter 36 is a check valve assembly comprising a duckbill-type check valve 44 of conventional construction which is held in position within neck portion 36b by an internally threaded retainer ring 46 which is received over flange portion 36a. A threaded closure plug 48 is threadably received within retainer ring 46 in the manner best seen in FIG. 4. Duckbill valve 44 includes a yieldably deformable "bill" 44a which functions in the traditional manner illustrated in FIGS. 6 and 7, permitting fluid to flow inwardly in the direction of the arrows designated by the numerals 50 in FIG. 6, but blocking fluid flow in the opposite direction in the manner shown in FIG. 7. It is to be understood that various types of check valves of a character well known to those skilled in the art can be used in place of the duckbill valve 44.

Body portions, or structural support members 12a and 12b can be constructed of any suitable gas permeable, porous material such as Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE) and porous cellulose acetate. A suitable source of these materials is Porex Technologies of Fairburn, Ga. However, practice has shown that any porous plastic material including an open cell, porous sponge material which permits the free passage of gases therethrough is suitable. As described in the following paragraphs, to enable venting of gases from the fluid chamber, membranes 22 and 24 can also be constructed from a suitable gas permeable material.

In practice membranes 22 and 24 can be single layers or laminates and can be manufactured from several alternate materials including rubber, plastics and other thermo-plastic elastomers. These include latex, rubber polyisoprene, butyl rubber, nytrial rubber, other homopolymer, copolymers, mechanical poly blends and interpenetrating polymer networks. Examples of materials found particularly well suited for the construction of the high gas permeable membranes include silicon polymers which are castable into thin film membranes having high gas permeability. Depending upon the fluid to be dispensed from the apparatus, other materials of choice for fabricating the membranes include polyurethane-polysiloxane, copolymers, blends and IPNs (interpenetrating polymer network materials). In certain applications, low gas permeable membranes such as floro-silicons and floroelastomers may be desirable. Manufacturers of materials suitable for use in the construction of the distendable membranes 22 and 24 include Dow Chemical, 3M Company, General Electric, Mobay Chemical, Shell Oil Corporation, DuPont, and Union Carbide Corporation.

The previously mentioned vent means of the invention is adapted to provide for make-up air during liquid delivery so that an even outflow of solution from the apparatus is obtained. To permit the flow of gases between atmosphere and the interior of the apparatus, flange 38a of outlet adapter 38 is provided with circumferentially spaced apertures 38c which permit free flow of air toward fluid chambers 14a and 14b in the manner shown by the arrows 51 in FIG. 7. In practice an oxygen impermeable sterile barrier patch 53 is removably affixed to flange 34 so as to cover apertures 38c.

By referring to FIG. 8, it can be seen that the encapsulating means, shown here as an outer barrier which surrounds the body portions 12a and 12b is perforated in the area of the apertures 38c provided in the flange 38. These apertures in the outer barrier permit air from atmosphere to flow into the porous body portions 12a and 12b in the manner shown by the arrows in FIG. 7 and designated by the numeral 51.

Turning to FIG. 9, the encapsulating means or outer barrier in the embodiment of the invention there shown comprises an outer paper wrap 42 covering an inner metalized wrap or encapsulation material 41. The outer barrier or encapsulating means can take several forms so long as it produces an oxygen impermeable, antimicrobial leak-free aseptic container. For example, the encapsulation means can comprise a barrier laminate structure which is made up of a plurality of specific high-strength polymer resin layers which effectively prevent formation of pin holes or cracking of oxygen barrier layers during package formation. One type of oxygen impermeable, leak-free container material is disclosed in U.S. Pat. No. 4,983,431 issued to Gibbons et al. Disclosures in this patent relating to leak-free packaging are also applicable to the encapsulation means of the aseptic package of the present invention. U.S. Pat. No. 3,998,378 issued to Vetten describes methods of fabricating a folding box having a liquid tight cemented bottom and improved stability. Techniques discussed in the Vetten patent can also be used in the construction of the outer barrier or encapsulating means of the present invention. To patents cited in Gibbons, et al. and Vetten are also pertinent to the construction of the encapsulation barrier of the present invention. Other pertinent prior art United States patents include U.S. Pat. No. 4,239,150 issued to Schadowski, et al., U.S. Pat. No. 4,254,693 issued to Shadowsski, et al., and U.S. Pat. No. 4,287, 247 issued to Reil, et al. The teachings of these prior art patents and the patents cited therein are more than adequate to inform those skilled in the art of the various techniques and materials that can be used in fabricating the encapsulating means, including oxygen impermeable aseptic containers, of the invention.

Turning now to FIGS. 4 and 7, it is to be observed that outlet port 34 is initially closed by a frangible diaphragm 56 which form an integral part of the outlet adapter 38. It is also to be noted that neck 38b of outlet adapter 38 is internally threaded with threads 58 which are adapted to threadably receive external threads 60 provided on the delivery spike assembly 40. Delivery spike assembly 40 includes an outwardly extending, generally cylindrically shaped portion 40a that terminates in a sharp spike or point 40b'. Point 40b is adapted to pierce frangible membrane 56 when the delivery spike is threadably connected with the outlet port assembly 34 in the manner illustrated in FIG. 7. An elastomeric O ring 64 is received within a groove 65 provided in cylindrical portion 40a and sealably engages the internal walls of neck 38b in the manner shown in FIG. 7. This prevents leakage of fluid from the pressurized container past the delivery spike and to the outside of the container.

Also forming a part of the delivery spike assembly of this form of the invention is a tubular conduit C that communicate with an external flow rate control means shown here as a cylindrical housing 65 having contained therewithin a porous mass of material 67 such as porous teflon, through which the discharging liquid must flow. Flow rate can be precisely controlled by proper selection of the material 67 in a manner well known to those skilled in the art.

Figure 6:
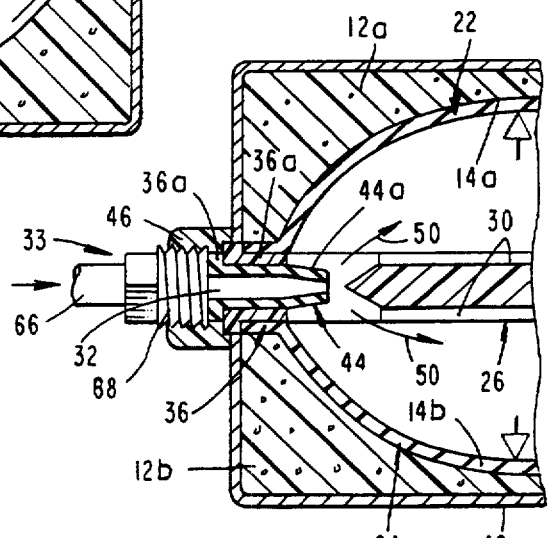
FIG. 6 is a fragmentary side-elevational, cross-sectional view of the fill port of the device.

In using the apparatus of the present invention, plug 48 is first removed and threadably inserted in its place is a fill tube 66 having a threaded fitting 68 which is receivable within retaining ring 46 (FIG. 6). In the aseptic filling process, the nutrient solution to be delivered to the patient is introduced through the check valve 44. The fluid being introduced will impinge upon membranes 22 and 24 causing them to distend from a first at rest position shown in FIGS. 4 and 5, wherein the central portions of the membranes are in proximity with support member 26, to a second distended position shown in FIGS. 6 and 7, wherein the central portions of the membranes are in proximity with the internal walls defining cavities 14a and 14b. Where permeable elastomeric membranes are used, gas in the solution being introduced into the carton can pass through the membranes 22 and 24 and migrate to porous foam blocks 12a and 12b with subsequent venting at time of use to atmosphere through orifices 38c. It is to be understood that distention of the membranes from the first to the second position creates internal stresses of predetermined direction and magnitude in the specifically tailored thin films of elastomeric membranes which tend to uniformly return them to their original, non-distended position shown in FIGS. 4 and 5.

So long as frangible diaphragm 56 is in tact, the beneficial agent or solution to be delivered to the patient will remain within the device. However, as soon as the diaphragm is ruptured by the delivery spike 40, the controllably stressed elastomeric membranes 22 and 24 will attempt to return to their original, non-distended configuration and will controllably and uniformly force the fluid outwardly through the delivery passageway 62 of the delivery spike into tube 63 and toward the patient in the direction of the arrow 64 shown in FIG. 7.

In certain applications, the retaining ring 46 and check valve assembly 44 can be recessed into body portions 12a and 12b so that after aseptic filling of the carton is complete, the outer most barrier of the encapsulation means can be folded over the check valve assembly in a manner to effectively seal it relative to atmosphere.

Referring now to FIGS. 10a, 11 and 12, another form of the liquid delivery apparatus of the present invention is there illustrated. This form of the invention is similar in most respects to the form of the invention described in the preceding paragraphs. Accordingly like numbers have been used to identify like components. The principal differences between this latter embodiment of the invention and the former embodiment resides in the provision of a differently configured check valve assembly 80 as well as differently configured distendable membrane assemblies 84.

The check valve assembly of this latter embodiment of the invention comprises an outer sleeve 86 which is receivable within fluid inlet 32. Provided proximate the outboard end of sleeve 86 is a flange 88 which is bondably interconnected with flange 36a of the inlet adapter 36. The check valve member of this alternate form of the invention comprises a generally cylindrically shaped member 90 having a body portion 92 and a reduced diameter neck portion 94. A shoulder 96 is formed at the junction of neck portion 94 and body portion 92. Check valve member 90 is reciprocally movable within sleeve 86 from an outward sealing position wherein shoulder 96 sealably engages an internal shoulder provided in member 88 to a retracted position wherein liquid will be permitted to flow through inlet port 32 and into pressural communication with the distendable membrane assemblies 84 of this form of the invention. It should be understood that once the device is pressurized by the filling of the nutritional fluids, the check valve member 90 will be urged into a sealing forward position blocking liquid flow outwardly through the inlet port 32. However, during the filling operation, the check valve member is movable rearwardly of sleeve 86 so as to permit fluid flow through a plurality of circumferentially spaced fluid flow passageways 97 provided in check valve member 90 (FIG. 11).

Turning now to FIG. 10a, it is to be noted that each of the distendable membranes of this later form of the invention comprises a laminate structure made up of a plurality of layers of elastomeric material 84a, 84b and 84c. This assemblage functions in much the same way as earlier described distendable membranes 22 and 24. However, by constructing each of the stored energy members from a composite of several distinct thin films or layers, the elastic characteristic of the stored energy means can be precisely tailored and can be uniquely constructed to function not only as a fluid driving medium but also as a gas permeability valve. The selective arrangement of the different films that make up the stored energy means, each with its own ascending permeability constant, will dictate the direction of flow of various gases and vapors. Vapors contained within the solution introduced into the device can pass through the stored energy means in one direction while external gases will be precluded from negative migration into the reservoir.

The solution contained within the device is delivered to the patient through the delivery spike assembly 40 in the same manner as was described in the discussion of the previous embodiment. Similarly, make-up air is supplied by the vent means through apertures 38(c) in the manner discussed in the preceding paragraphs.

Referring now to FIGS. 13, 14, 15 and 16, still another form of the liquid delivery apparatus of the present invention is there illustrated. This latest form of the invention is also similar in many respects to the invention described in the preceding paragraphs. Accordingly, like numbers are used in these figures to identify like components.

Figure 13:
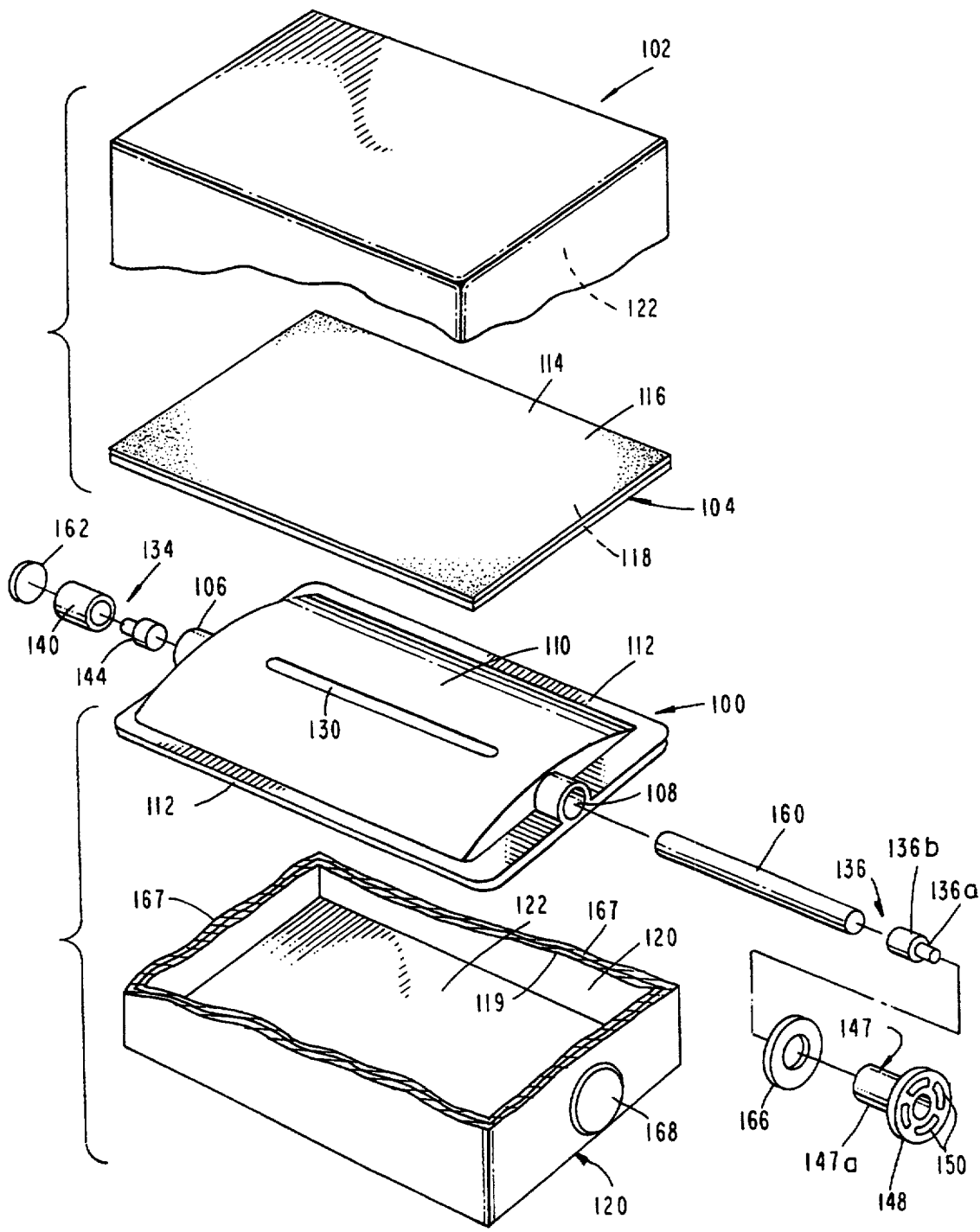
FIG. 13 is a generally perspective exploded view of another embodiment of the nutrient delivery apparatus of the invention.
Figure 20:
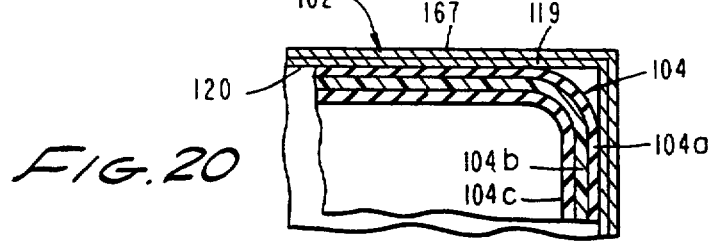
FIG. 20 is a fragmentary cross-sectional view of area 20—20 of FIG. 15.

As best seen by referring to FIG. 13, the liquid delivery apparatus of this latest form of the invention comprises a base assembly 100, a carton-like body 102 within which the base assembly is encapsulated and a distendable membrane assembly 104 which overlays base assembly 100. Base assembly 100 has a fluid inlet and a fluid outlet 106 and 108 respectively and includes a central, convex portion 110 which is circumscribed by an edge portion 112. Distendable membrane assembly 104 also includes a central portion 114 which is circumscribed by upper and lower edge portions 116 and 118 respectively. As shown in FIG. 20, distendable membrane assembly 104 can be made up of at least two, but preferably a plurality of thin film distendable membranes 104a, 104b and 104c. For example, layer 104a which is distal to the reservoir comprises a thin film elastomer of a first thickness and a first permeability. On the other hand, layer 104c which is proximal to the reservoir, comprises a thin elastomer film of a second thickness and a second permeability. This film is uniquely selected to be compatible in all respects with the fluid contined within the reservoir. Layer 104b can be of yet another thickness and permeability and, if desired can also have different perm-select characteristics. As previously described, the selective arrangement of the different films, each with its own individual permeability constants in ascending order, will dictate the direction of flow of selected gases and vapors through the stored energy means.

Figure 15:
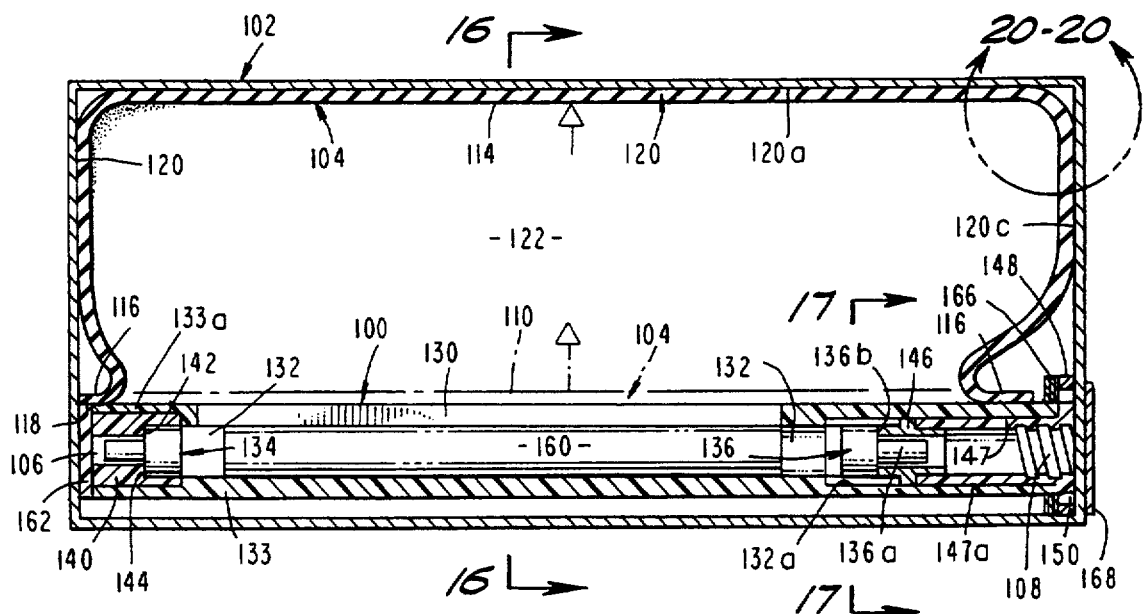
FIG. 15 is a cross-sectional view taken along lines 15—15 of FIG. 14.

Turning now to FIGS. 15, 16, and 20, it can be seen that body assembly 102 includes an inner barrier member 119 having internal surfaces 120 which define a cavity or fluid reservoir 122. Barrier member 119 is provided with end flaps (not shown) which can be folded over into the position shown in the drawings after the reservoir 122 is filled in the manner presently to be described. Distendable membrane assembly 104 is distendable from a first position wherein the central portion 114 thereof is in close proximity with the central portion 110 of base assembly 100 to a second distended position wherein central portion 114 is in close proximity with the upper internal walls 120a of body assembly or carton 102. The membrane assembly also moves into close proximity with the internal surfaces 120b of walls 120 of the carton (FIG. 16) and with the internal surfaces of end walls 120c (FIG. 15). As before, when the distendable membrane assembly 104 is distended from the first to the second position, internal stresses are developed within the membrane which tend to uniformly return it toward its first position in close proximity with the central portion 110 of base assembly 100.

Figure 14:
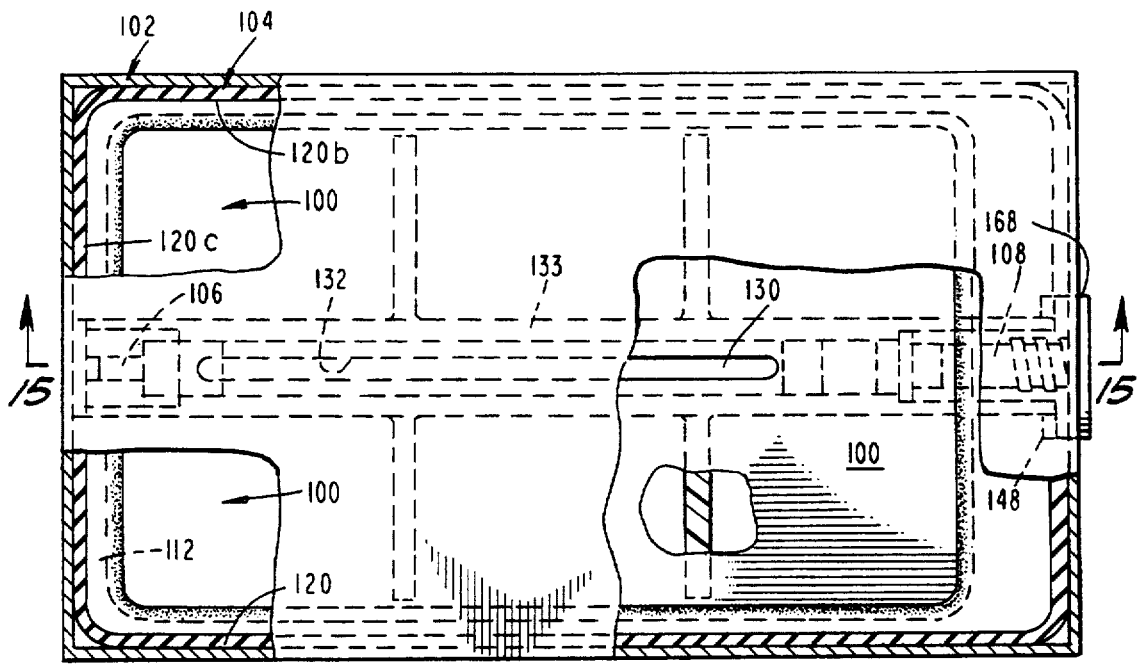
FIG. 14 is a plan view of the device partly broken away to show internal construction.

Referring to FIGS. 13, 14, and 16 it can be seen that base assembly 100 is provided with a longitudinally extending flow channel 130 which communicates with an internal longitudinally extending flow passageway 132 that extends between and interconnects together inlet 106 and outlet 108. As best seen in FIG. 16, flow passageway 132 is formed internally of a semitubular shaped, longitudinally extending protuberance 133 formed integrally with base assembly 100.

Disposed proximate the inlet portion of fluid passageway 132 is a check valve assembly generally designated by the numeral 134. A similar check valve 136 is disposed proximate the outlet portion of fluid passageway 132. Referring to FIG. 15, it can be seen that inlet check valve 134 is receivable within a cylindrically shaped retaining member 140 which is receivably within an enlarged diameter portion 133a of protuberance 133. Member 140 has an internal shoulder 142 adapted to engage an external shoulder 144 formed on check valve 134. When the check valve 134 is in the closed position shown in FIG. 15 wherein shoulder 144 is in engagement with internal shoulder 142 of member 140, the flow of fluid inwardly into fluid passageway 132 is blocked.

Check valve 136 which is positioned proximate the outlet of fluid passageway 132 is held in position within the fluid passageway by a retainer member 146 which is disposed within passageway 132 in engagement with an internally threaded outlet receptacle 147. Outlet receptacle 147 which comprises a part of the vent means of the invention, includes a tubular body portion 147a and flange portion 148 having a plurality of circumferentially spaced apertures 150 (FIG. 13). As best seen by referring to FIG. 15, the reduced diameter portion 136a of check valve 136 is movably receivable within a bore provided in retainer member 146. With the shoulder 136b of the check valve 136 in sealable engagement member 146 fluid flow through passageway 132 in a direction toward outlet 108 is effectively blocked.

Also disposed within fluid passageway 132, intermediate check valves 134 and 136, is a flow rate control means shown here as an elongated, generally cylindrically shaped porous filter member 160. Member 160 can be constructed of any inert porous material such as a ceramic or porous plastic, fluid permeable material and can be tailored to provide a precise rate of fluid flow through passageway 132 in a manner well known to those skilled in the art.

As best seen in FIG. 18, at the outlet portion of the apparatus tubular body portion 147a of receptacle 147 is positioned within an enlarged diameter portion 132a of flow passageway 132 with flange 148 of member 147 positioned against base assembly 100. A hydrophobic filter vent means for venting air but not moisture is here shown as disk shaped member 166 which is appropriately bonded to the interior surfaces of flange 148 of member 147 in the manner shown in FIG. 18. A material such as hydrophobic PTFE, polytetrafluoroethylene incorporating laminated polypropylene or hydrophobic acrylic copolymer supported on nylon nonwoven substrates is suitable for the construction of member 166.

With outlet check valve 136 in a closed position, chamber or reservoir 122 is filled with the selected feeding solution by inserting an appropriate filling conduit into the inlet portion of the device (not shown). The filling conduit is adapted to move check valve 134 inwardly permitting the feeding solution to flow into passageway 132 and then outwardly of channel 130 where it impinges on membrane assembly 104 with sufficient pressure to distend it in to the position shown in FIGS. 15 and 16.

After reservoir 122 has been filled, the pressure of the solution within the reservoir will maintain both the inlet and outlet check valves 134 and 136 in the closed position shown in FIG. 15. Following filling of the reservoir, a retainer disk 162 is positioned over the inlet or filling port 106 and the end flaps of barrier member 119 and folded over to hold disk 162 as well as outlet receptacle 147 in position. This done, an outer barrier layer 167 (FIGS. 13 and 20) is emplaced over the entire assemblage so as to completely encapsulate it within a sealed oxygen impermeable, antimicrobial, leak-free aseptic container of the character previously described herein. Finally a disk shaped metalized seal 168 is positioned over the outer barrier in the proximity of the vent means or flange 148 of outlet receptacle 147. The apparatus of the invention is now ready for shipment storage and subsequent use in the field.

The feeding solution contained within reservoir 122 is accessed by a delivery spike 170 of a construction similar to delivery spike 140 of the earlier described embodiments. As shown in FIG. 19, delivery spike 170 comprises a finger grip portion 172, a flange portion 174 and an externally threaded neck portion 176. For a purpose presently to be described, a plurality of circumferentially spaced, outwardly extending pointed protuberances 177 are provided on flange portion 174.

Turning now to FIG. 21, upon piercing the metalized seal 168 and the barrier layers 119 and 167, threads provided on neck portion 176 of the delivery spike can be moved into threadable engagement with the internal threads 181 provided on outlet receptacle 147 in the manner shown in FIG. 21. As the neck portion of the delivery spike advances into receptacle 147, the end of the neck portion will engage outlet check valve 136 moving it into an open position which will permit liquid within reservoir 122 to flow through channel 130, into passageway 132 and then into central passageway 180 provided in the delivery spike. As elastomeric O ring 182 is carried by neck portion 176 for engagement with the internal wall of the outlet receptacle to prevent leakage of the feeding solution past the delivery spike.

As illustrated in FIG. 21, as the check valve 136 is moved into the open position, protuberances 177 will pierce metalized seal 168 and will extend into vent apertures 150 thereby creating openings which permit make-up air to flow into the device as the feeding solution is introduced into the patient.

Turning now to FIGS. 22 through 30, still another form of the invention is there shown. The apparatus here shown is similar to that shown in FIGS. 1 through 9 and like numbers have been used to identify like components. The major difference between the embodiment of the invention shown in these figures and that described in connection with FIGS. 1 through 9 resides in the fact that the energy source for expelling the fluid is totally different. More particularly, in this latest form of the invention, the distendable membranes 22 and 24 have been replaced with deformable barrier like members 200a and 200b which form an interface between the new energy source and the fluid entering reservoirs "R" of the unit (see FIGS. 27 and 28). Members 200a and 200b can be constructed of a number of materials, such as various elastomers, and are generally the same shape as is the previously described distendable membranes 22 and 24. In this latest form of the invention, the stored energy means, which may take the form of an expandable polymer, is contained within chambers provided in slightly differently configured, cooperating body portions.

Figure 24:
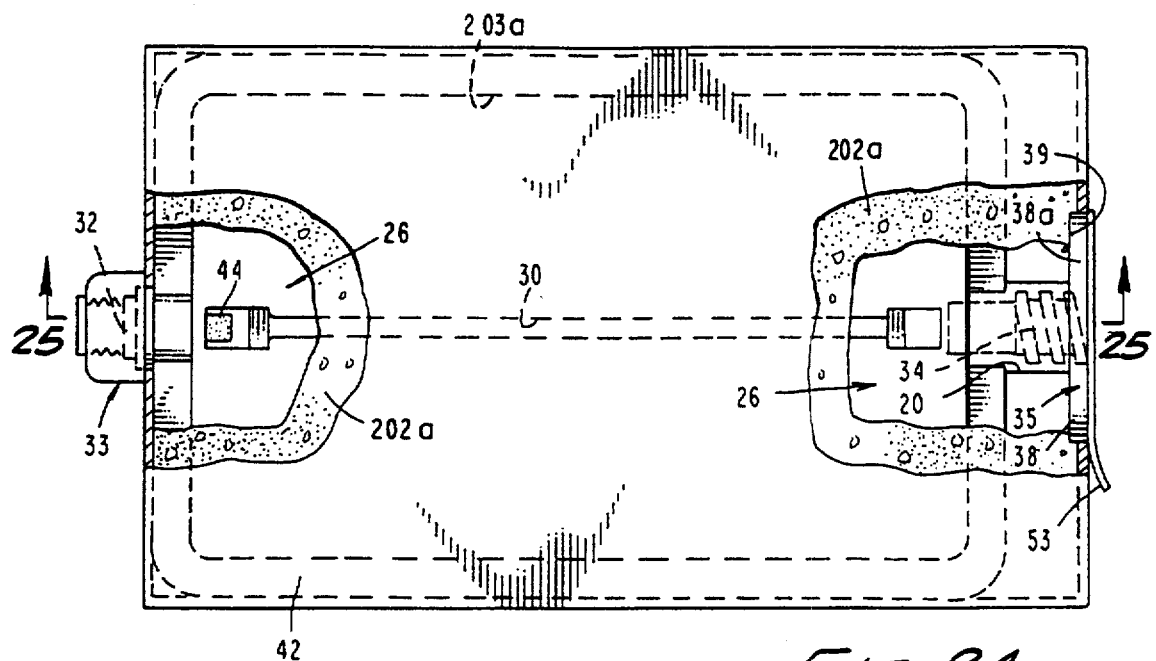
FIG. 24 is a top-plan view of the device partly broken away to show internal construction.

Referring particularly to FIGS. 22, 23 and 24, as before, the liquid delivery apparatus of the latest form of the invention comprises a body made up of cooperating first and second portions here designated as 202a and 202b respectively. As can best be seen by referring to FIG. 26, each body portion includes internal walls defining chambers 203a and 203b respectively with each chamber being circumscribed by an edge 204a and 204b respectively. The new stored energy means is disposed within chambers 203a and 203b and is here shown as expandable, cellular like members 207a and 207b. The details of the construction of these members will be described presently. Each body portion is also provided at either end with semi-circular shaped, indexable openings generally designated by the numerals 18 and 20.

First deformable member 200a is provided with an edge portion 205a which is disposed in engagement with edge portion 204a of first body portion 202a. Second deformable member 200b has an edge portion 205b which is disposed in engagement with edge portion 204b of second body portion 202b. Each of the deformable members, the unique character of which will presently be described, includes a central portion which spans chambers 203a and 203b formed in the cooperating body portions.

Once again a rigid support, or ullage member 26 is disposed between members 200a and 200b. Support member 26 is of identical construction and function as that previously described herein.

Also comprising a part of the liquid delivery apparatus of this latest form of the invention is a fluid delivery means which is in communication with the fluid outlet port of the apparatus. The fluid delivery means functions to deliver fluid to the patient in the same manner as previously described and comprises a delivery spike assembly 40, which is adapted to cooperate with the fluid outlet port assembly 35.

Figure 26:
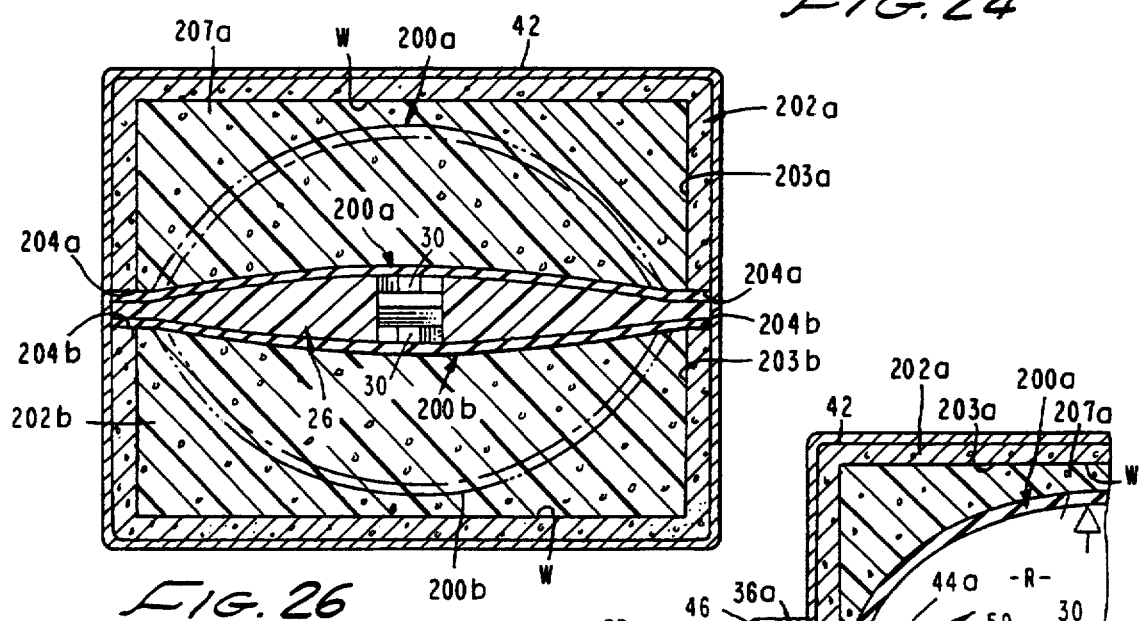
FIG. 26 is a cross-sectional view taken along lines 26—26 of FIG. 25.
Figure 30:
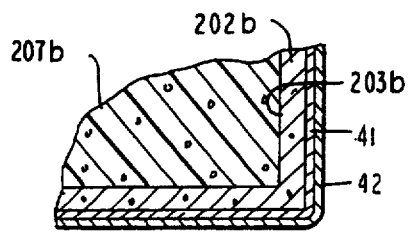
FIG. 30 is a fragmentary cross-sectional view illustrating one form of the multi-film barrier construction of the device.

As best seen by referring to FIGS. 23 and 26, body portions 202a and 202b are once again encapsulated by the highly important oxygen non-permeable encapsulating barrier means shown here as thin layers of material 41 and 42 sealably surrounding body portions 202a and 202b (FIG. 30). The character of this sealing material and the manner in which it is applied is precisely as was discussed in connection with the first form of the invention shown in FIGS. 1 through 9.

As was previously the case, body portions, or structural support members 202a and 202b can be constructed of any suitable gas permeable, porous material such as Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE) and porous cellulose acetate. A suitable source of these materials is Porex Technologies of Fairburn, Ga.

In practice deformable members 200a and 200b can be single layers or laminates and can be manufactured from a number of different materials including rubber, plastics and other elastomers, including thermo-plastic elastomers. Materials particularly desirable for fabricating members 200a and 200b include silicones polyurethane-polysiloxane, and other copolymers, blends and IPNs (interpenetrating polymer network materials).

Turning to FIG. 30, the encapsulating means or outer barrier in the embodiment of the invention there shown is the same as earlier described herein and comprises an outer paper wrap 42 covering an inner metalized wrap or encapsulation material 41. This highly important outer barrier or encapsulating means can take several forms so long as it produces an oxygen impermeable, anti-microbial leak-free aseptic container. For example, the encapsulation means can comprise a barrier laminate structure which is made up of a plurality of specific high-strength polymer resin layers of the character previously described.

Prior to forming the barrier or encapsulating means about body portions 202a and 202b, the unique stored energy means of this latest form of the invention is emplaced within chambers 203a and 203b which here are generally U shaped in cross section. As previously mentioned, the stored energy means is here provided as elastic, cellular foam like resilient sponge members 207a and 207b. Members 207a and 207b can be constructed from a wide variety of materials, including a number of flexible cellular polymers. Materials that are particularly attractive for this application include polyurethane, latex foam rubber, cellular rubber, various polyolefin foams, PVC foams, epoxy foams, urea formaldehyde, silicon foam, fluropolymer foam, and other elastic syntatic foams and similar materials of a character well understood by those skilled in the art. Members 207a and 207b can be monolithic or they can be constructed from homogenous or nonhomogenous foam or foam laminates having the same or different characteristics. They may be separate from or formed integrally with deformable members 200a and 200b. In either event the deformable members act as the interface between the energy source and the liquid to be expelled from the device.

Figure 27:
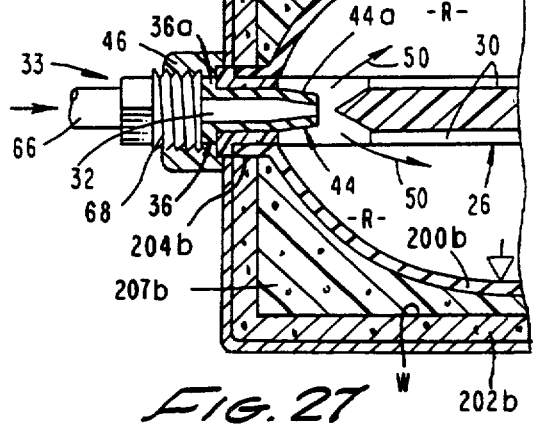
FIG. 27 is a fragmentary, side-elevational, cross-sectional view of the fill port of the device.

In using the apparatus of this latest form of the invention, plug 48 is first removed and threadably inserted in its place is a fill tube 66 having a threaded fitting 68 which is receivable within retaining ring 46 (FIG. 27). In the aseptic filling process, the nutrient solution to be delivered to the patient is introduced through the check valve 44. The fluid being introduced will impinge upon deformable members 200a and 200b causing them to deform from a first at rest position shown by the solid lines in FIG. 26 to the distended position shown by the phantom lines in FIG. 27. In this expanded position, the stored energy members 207a and 207b have been compressed and the central portions of the deformable members reside in close proximity walls "W" of chambers 203a and 203b. Where permeable deformable members are used, gas in the solution being introduced into the carton can pass through the members and migrate to the porous foam blocks which comprise body portions 202a and 202b with subsequent venting at time of use to atmosphere through orifices 38c. It is to be understood that deformation of members 200a and 200b from the first to the second position creates internal stresses of predetermined direction and magnitude in the specifically tailored energy sources or sponge like members 207a and 207b which tend to uniformly return these members toward their original, non-compressed configuration proximate ullage member 26.

So long as frangible diaphragm 53 is in tact, the beneficial agent or solution to be delivered to the patient will remain within the device. However, as soon as the diaphragm is ruptured by the delivery spike 40, simultaneously permitting the system to vent, the controllably stressed sponge like energy source members 207a and 207b will attempt to return to their original, non-compressed configuration and will act upon deformable members 200a and 200b to controllably and uniformly force the fluid outwardly through the delivery passageway 62 of the delivery spike into tube 63 and toward the patient in the direction of the arrow 64 shown in FIG. 28.

In certain applications, the stored energy means, or members 207a and 207b can be pre-compressed and emplaced within chambers 203a and 203b in a pre-stressed configuration. In this instance, at the time of delivery, the solution will be expelled from the device as a result of the controlled expansion of the pre-compressed energy source members acting upon the deformable members, which, in turn, act upon the solution to force it outwardly of the dispensing means.

Referring now to FIGS. 31, 31A, and 32 still another form of the liquid delivery apparatus of the present invention is there illustrated. This form of the invention is similar in most respects to the form of the invention described in the preceding paragraphs and includes the unique stored energy source described in the immediately preceding section. This being the case, once again like numbers have been used to identify like components. The principal differences between this latter embodiment of the invention and the embodiment just described resides in the provision of a differently configured check valve assembly 80 as well as differently configured deformable member assemblies generally designated in FIG. 31A by the numeral 210.

The check valve assembly of this latter embodiment of the invention is of the character previously described and comprises an outer sleeve 86 which is receivable within fluid inlet 32. Provided proximate the outboard end of sleeve 86 is a flange 88 which is bondably interconnected with flange 36a of the inlet adapter 36. The check valve member of this alternate form of the invention and its mode of operation is as described in connection with the form of the invention shown in FIGS. 10 through 12.

Turning particularly now to FIG. 31A, it is to be noted that each of the deformable members of this later form of the invention comprises a laminate structure made up of a plurality of layers of elastomeric material 210a, 210b and 210c. This assemblage functions in much the same way as the earlier described deformable members 200a and 200b. However, by constructing each of the members from a composite of several distinct thin films or layers, the characteristics of the members can be precisely tailored and can be uniquely constructed to function not only as an interface between the liquid medium and the stored energy source, but also as a gas permeability barrier. The selective arrangement of the different films that make up the assemblage, each with selected permeability constants, will control the direction and inhibit the flow of various gases and vapors. The film layer disposed proximate the liquid must, of course, be compatible with the liquid in all respects.

The solution contained within the device is delivered to the patient through the delivery spike assembly 40 by the deformable members acting on the stored energy means, or members 207a and 207b, in the same manner as was described in the discussion of the previous embodiment. Similarly, make-up air is supplied by the vent means through apertures 38(c) in the manner discussed in the preceding paragraphs.

Referring now to FIGS. 34 through 42, yet another form of the liquid delivery apparatus of the present invention is there illustrated. This latest form of the invention is also similar in many respects to the invention described in the preceding paragraphs. Accordingly, like numbers are used in these figures to identify like components.

Figure 34:
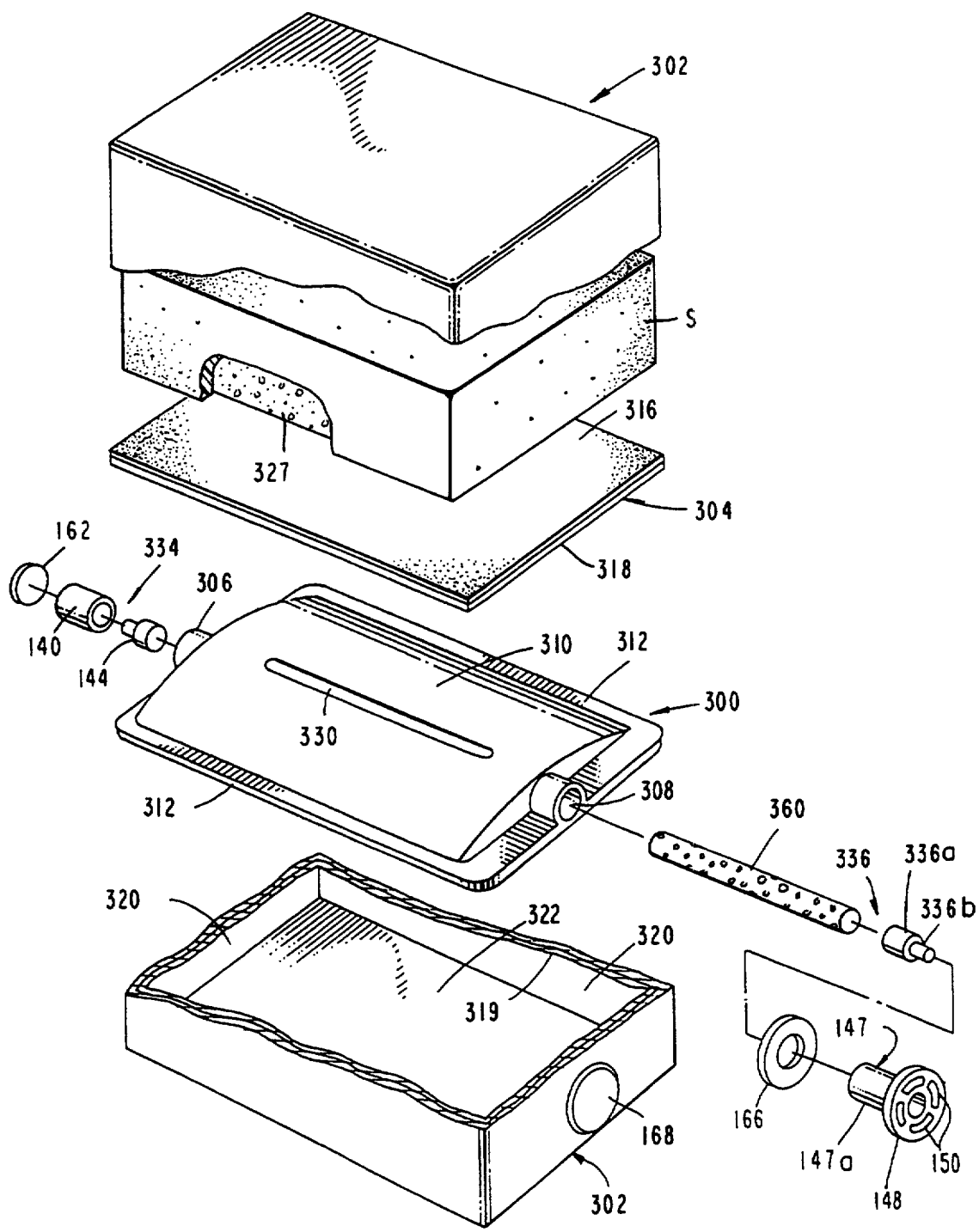
FIG. 34 is a generally perspective exploded view of yet another embodiment of the nutrient delivery apparatus of the invention.
Figure 37:
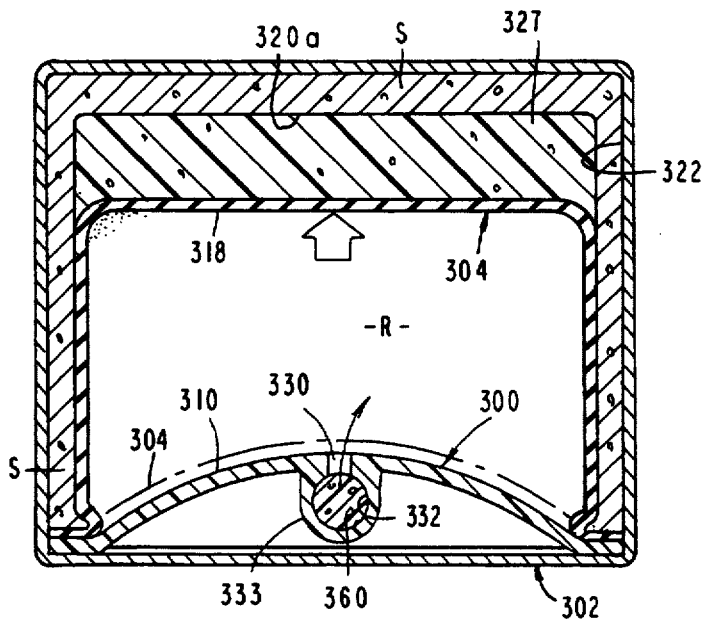
FIG. 37 is a cross-sectional view taken along lines 37—37 of FIG. 36.
Figure 39:
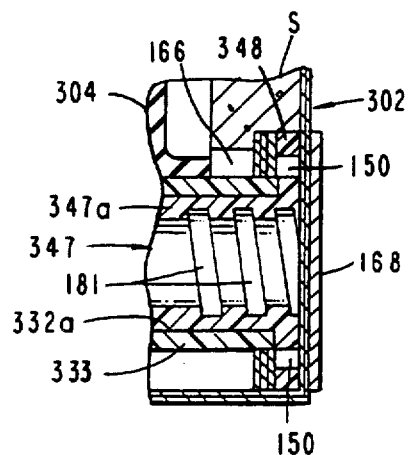
FIG. 39 is an enlarged fragmentary view of the outlet portion of the device.
Figure 38:
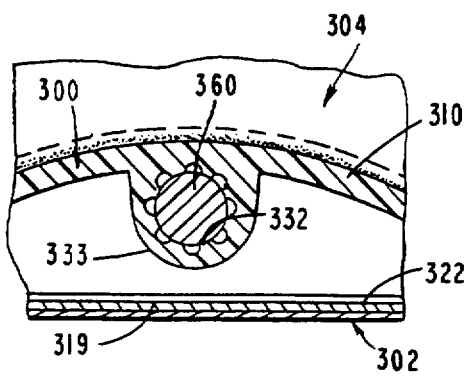
FIG. 38 is a cross-sectional view taken along lines 38—38 of FIG. 36.
Figure 40:
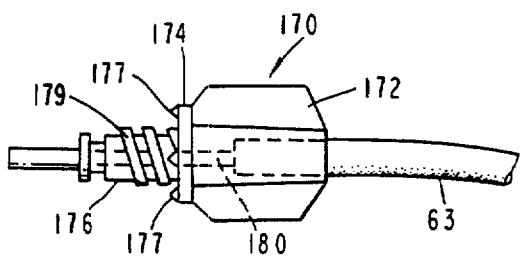
FIG. 40 is an enlarged fragmentary view of the delivery spike of this latest embodiment.
Figure 42:
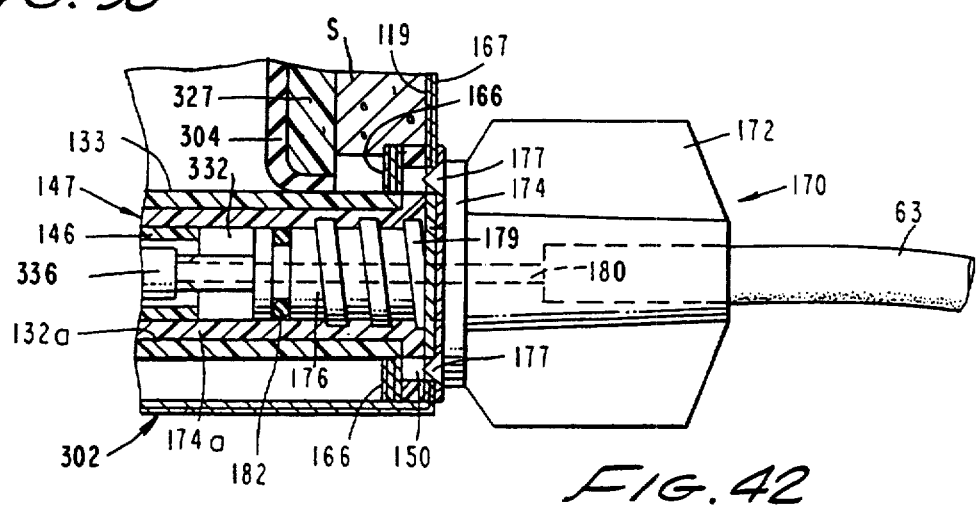
FIG. 42 is an enlarged fragmentary cross-sectional view of the delivery spike mated with the outlet port of the device.

As best seen by referring to FIG. 34, the liquid delivery apparatus of this latest form of the invention comprises a base assembly 300, a carton-like body 302 within which the base assembly is encapsulated and a deformable assembly 304 which overlays base assembly 300. Base assembly 300 has a fluid inlet and a fluid outlet 306 and 308 respectively and includes a central, convex portion 310 which is circumscribed by an edge portion 312. Deformable assembly 304 also includes a central portion 314 (FIG. 36) which is circumscribed by upper and lower edge portions 316 and 318 respectively. As shown in FIG. 41, deformable assembly 304 can be made up of at least two, but preferably a plurality of thin film membranes 304a, 304b and 304c each having selected permeability constants and material characterics. For example, layer 304a can comprise a thin film elastomer of a first thickness and a first permeability. On the other hand, layer 304c can comprise a thin elastomer film of a second thickness and a second permeability. Layer 304b can be of yet another thickness and permeability and, if desired can also have different perm-select characteristics.

In this latest form of the invention, body assembly 302 includes an inner barrier member 319 having internal surfaces 320 which define a chamber 322 (see FIG. 34). Disposed interiorly of chamber 322 is a porous cellular structural member "S" against which the expandable member resides. Assembly 304 is deformable from a first position, a shown by the phantom lines in FIG. 36, wherein the central portion 314 thereof is in close proximity with ulluge member 310 of base assembly 300, to a second distended position as shown by the solid lines in FIG. 36, wherein central portion 314 is in close proximity with the upper internal walls 320a of body assembly or carton 302. As before, when the deformable assembly is deformed from the first to the second position, the stored energy source, or sponge like member 327, which is disposed interiorly of structural member "S" is compressed in a manner such that internal stresses are developed therewithin which tend to uniformly return it toward its first position in close proximity with the ullage member 310 of base assembly 300.

As before, base assembly 300 is provided with a longitudinally extending flow channel 330 which communicates with an internal longitudinally extending flow passageway 332 that extends between and interconnects together inlet 306 and outlet 308. As shown in the drawings, flow passageway 332 is formed internally of a semitubular shaped, longitudinally extending protuberance 333 formed integrally with base assembly 300.

As was the case with the form of the invention shown in FIGS. 13 through 16, a check valve assembly is disposed within fluid passageway 332 and is generally designated by the numeral 334 (FIG. 34). A similar check valve 336 is disposed proximate the outlet portion of fluid passageway 332. These check valves are of the same construction and operation as was previously described.

Also disposed within fluid passageway 332, intermediate check valves 334 and 336, is a flow rate control means shown here as an elongated, generally cylindrically shaped porous filter member 360. Member 360 is also of the construction and operation as previously described can be and can be tailored to provide a precise rate of fluid flow through passageway 332 in a manner well known to those skilled in the art.

As before, at the outlet portion of the apparatus tubular body portion 347a of receptacle 347 is positioned within an enlarged diameter portion 332a of flow passageway 332 with flange 348 of member 347 positioned against base assembly. A hydrophobic filter vent means for venting air but not moisture is here shown as disk shaped member 166 which is appropriately bonded to the interior surfaces of flange 348 of member 347 in the manner shown in FIG. 18. A material such as hydrophobic PTFE, polytetrafluoroethylene incorporating laminated polypropylene or hydrophobic acrylic copolymer supported on nylon nonwoven substrates is suitable for the construction of member 166.

With outlet check valve 336 in a closed position, chamber or reservoir "R" is filled with the selected feeding solution by inserting an appropriate filling conduit into the inlet portion of the device (not shown). The filling conduit is adapted to move check valve 334 inwardly permitting the feeding solution to flow into passageway 332 and then outwardly of channel 330 where it impinges on deformable assembly 304 with sufficient pressure to, in turn, compress the stored energy source member 327 so as to distend it in to the position shown in FIG. 37.

After the filling step is completed, the pressure of the solution within the reservoir "R" will maintain both the inlet and outlet check valves 334 and 336 in the closed position in the manner previously described. Following filling of the reservoir "R", an outer barrier layer is emplaced over the entire assemblage in the manner previously described so as to completely encapsulate it within a sealed oxygen impermeable, antimicrobial, leak-free aseptic container of the character previously described herein.

The feeding solution contained within reservoir "R" is accessed by a delivery spike of a construction similar to that of the earlier described embodiments and the solution is dispensed by the expandable member acting on the deformable member which, in turn, acts on the solution.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A liquid delivery apparatus comprising:
   (a) a housing having internal walls defining a chamber;
   (b) a support disposed within said housing having a central portion, an edge portion circumscribing said central portion and including a liquid passageway in communication with said chamber of said housing, said liquid passageway having an inlet and an outlet;

(c) a deformable member having a central portion circumscribed by an edge, said central portion spanning said central portion of said support with said edge being disposed in engagement with said edge portion of said support, said deformable member being deformable from a first position wherein said central portion is in close proximity with said support to a second position wherein said central portion is in close proximity of said internal walls defining said chamber;

(d) an expandable member disposed within said chamber for engagement with said deformable member for moving said deformable member toward said second position;

(e) means for sealably encapsulating said housing, said deformable member and said support, said means comprising an oxygen impermeable barrier surrounding said housing; and (f) means for permitting the flow of gases between atmosphere and said chamber of said housing as said distendable membrane moves from said second position to said first position.

2. A liquid delivery apparatus as defined in claim 1 further including flow rate control means disposed interiorly of said liquid passageway of said support for controlling the rate of flow of fluid through said passageway.

3. A liquid delivery apparatus as defined in claim 1 further including a pair of porous bodies disposed interiorly of said chamber, each said body having internal walls defining a cavity, said support being disposed between said porous bodies.

4. A liquid delivery apparatus as defined in claim 3 further including a second deformable member having a central portion deformable from a first position in proximity with said support to a second position in proximity with said internal walls of one of said porous bodies.

5. An apparatus as defined in claim 4 further including a second expandable member disposed proximate said second deformable member for urging said second deformable member toward said second position.

6. An apparatus as defined in claim 5 in which said deformable member comprise multi-layers of elastic material.

7. An apparatus as defined in claim 6 further including check valve means disposed within said inlet of said support for permitting fluid flow in a first direction and for blocking fluid flow in a second direction.

8. An apparatus as defined in claim 7 further including a frangible diaphragm for closing said outlet of said support.

9. An apparatus as defined in claim 8 further including fluid delivery means having coupling means for interconnection with said outlet of said support and spike means for rupturing said frangible diaphragm upon interconnection of said coupling means with said outlet.

10. A liquid delivery apparatus comprising:

(a) a porous body, including first and second portions, each said portion comprising:

(i) internal walls defining a chamber, said chamber being circumscribed by an edge;

(ii) first and second spaced apart openings in communication with said chamber;

(b) a first deformable member having a central portion circumscribed by an edge, said central portion spanning the said chamber of said first body portion with said edge being disposed in engagement with said edge of said first body portion;

(c) a first expandable member disposed in said chamber of said first portion intermediate said internal walls thereof and said first deformable member for expanded engagement with said first deformable member;

(d) a second deformable member having a central portion circumscribed by an edge, said central portion spanning said chamber in said second body portion with said edge being disposed in engagement with said edge of said second body portion;

(e) a second expandable member disposed in said chamber of said second portion intermediate said internal walls thereof and said second deformable member for expanded engagement with said second deformable member;

(f) a fluid inlet port disposed within said first opening in said body portions;

(g) a fluid outlet port disposed within said second opening in said body portions;

(h) a support member disposed intermediate said first and second distendable membranes, said support member having a fluid passageway in communication with said fluid inlet and outlet ports; and (i) liquid delivery means in communication with said fluid outlet port for delivering fluid from said apparatus upon said first and second expandable members moving into expanded engagement with said first and second deformable members.

11. An apparatus as defined in claim 10 further including encapsulating means for sealably encapsulating said body.

12. An apparatus as defined in claim 11 in which said liquid delivery means includes flow control means disposed externally of said encapsulating means for controlling the rate of liquid flow to the patient and in which said fluid outlet port includes vent means for venting gases from said cavities to atmosphere.

13. An apparatus as defined in claim 12 in which said first and second deformable members are deformed from a first position wherein said central portions of said membranes are in proximity with said support member to a second position wherein said central portions of said membranes are in engagement with said first and second expandable members respectively.

14. An apparatus as defined in claim 12 in which deformation of said deformable members from said first to said second position compresses said first and second expandable members respectively to form internal stresses tending to return said members to an uncompressed configuration.

* * * * *